(12) United States Patent
Kanai et al.

(10) Patent No.: US 11,413,000 B2
(45) Date of Patent: Aug. 16, 2022

(54) X-RAY CT APPARATUS AND STORAGE MEDIUM

(71) Applicant: CANON MEDICAL SYSTEMS CORPORATION, Otawara (JP)

(72) Inventors: Eri Kanai, Otawara (JP); Hiroaki Miyazaki, Otawara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 10 days.

(21) Appl. No.: 17/170,958

(22) Filed: Feb. 9, 2021

(65) Prior Publication Data

US 2021/0251588 A1   Aug. 19, 2021

(30) Foreign Application Priority Data

Feb. 14, 2020   (JP) .............................. JP2020-023087

(51) Int. Cl.
*A61B 6/00* (2006.01)
*A61B 6/03* (2006.01)

(52) U.S. Cl.
CPC ............ *A61B 6/4488* (2013.01); *A61B 6/032* (2013.01); *A61B 6/4241* (2013.01); *A61B 6/461* (2013.01); *A61B 6/54* (2013.01)

(58) Field of Classification Search
CPC ..... A61B 6/4488; A61B 6/032; A61B 6/4241; A61B 6/461; A61B 6/54; A61B 6/58; A61B 6/488
See application file for complete search history.

(56) References Cited

U.S. PATENT DOCUMENTS

| 9,229,115 B2 | 1/2016 | Griesmer et al. |
| 2003/0016779 A1 | 1/2003 | Pohan et al. |
| 2005/0078795 A1 | 4/2005 | Kawabuchi |
| 2011/0222649 A1 | 9/2011 | Hashimoto et al. |
| 2013/0077745 A1 | 3/2013 | Wang et al. |

(Continued)

FOREIGN PATENT DOCUMENTS

| JP | 04-315985 A | 11/1992 |
| JP | 2003-130961 A | 5/2003 |
| JP | 2019-018021 A | 2/2019 |

OTHER PUBLICATIONS

Extended European Search Report dated Jul. 15, 2021 in corresponding European Patent Application No. 21156895.1, 7 pages.

*Primary Examiner* — Courtney D Thomas
(74) *Attorney, Agent, or Firm* — Oblon, McClelland, Maier & Neustadt, L.L.P.

(57) ABSTRACT

An X-ray CT apparatus according to an embodiment includes processing circuitry. The processing circuitry is configured to obtain initial temperature information of a photon counting detector before a main scan, information about the shape of a subject, and a scan condition of the main scan. The processing circuitry is configured to estimate a temperature change of the photon counting detector to be observed when the main scan is performed, on the basis of the initial temperature information, the information about the shape of the subject, and information about the scan condition of the main scan. The processing circuitry is configured to judge whether or not it is possible to perform the main scan, on the basis of the temperature change and the initial temperature information.

19 Claims, 15 Drawing Sheets

(56) References Cited

U.S. PATENT DOCUMENTS

2015/0076357 A1  3/2015  Frach
2019/0008474 A1* 1/2019  Sjolin .................... A61B 6/585
2019/0021687 A1  1/2019  Kato et al.

* cited by examiner

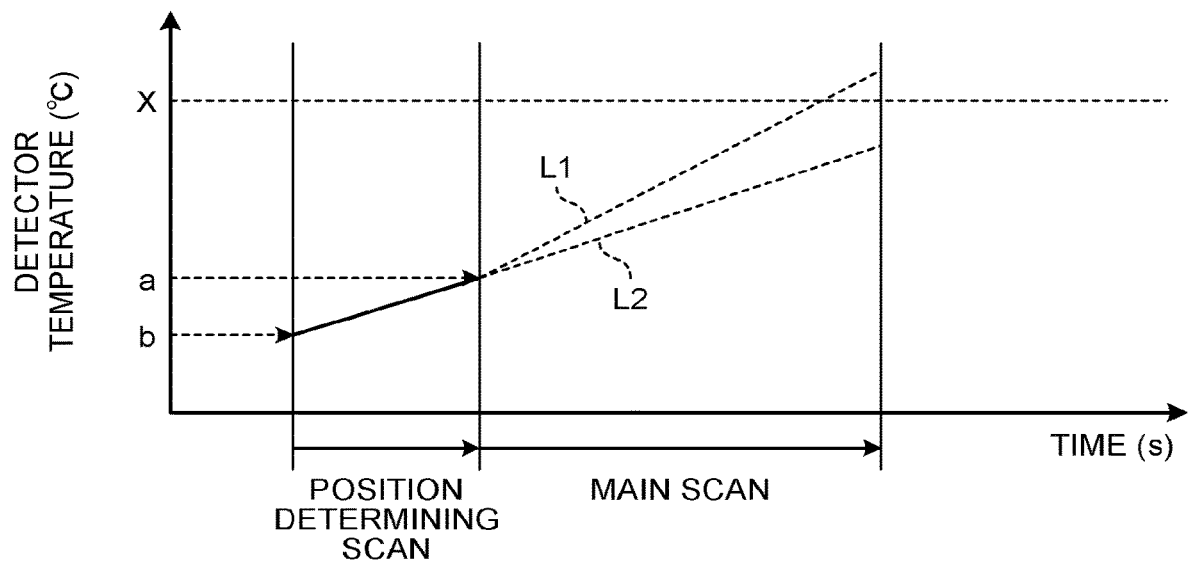

| TIME | TEMPERATURE CHANGE |
|---|---|
| t1 | -T5 |
| t2 | -T6 |
| t3 | -T7 |
| t4 | -T8 |
| t5 | -T9 |

FIG.8
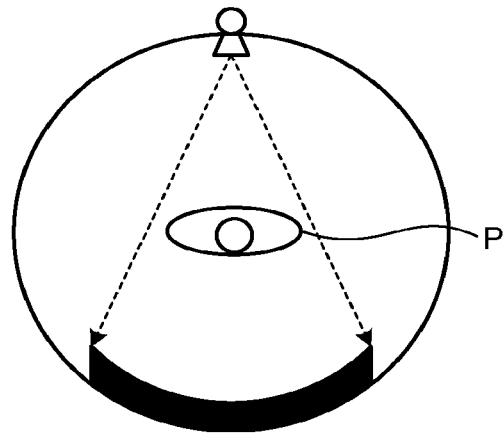
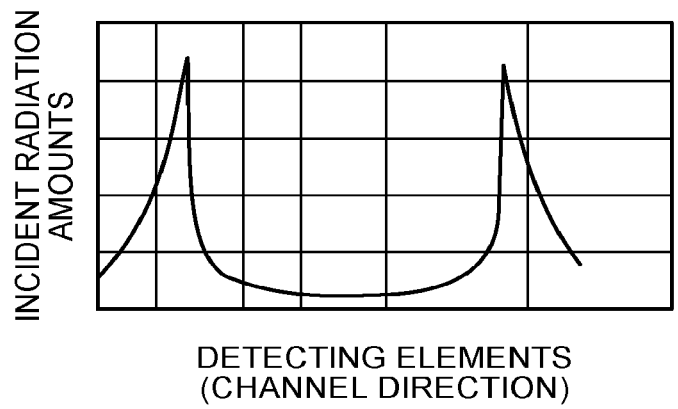
FIG.9
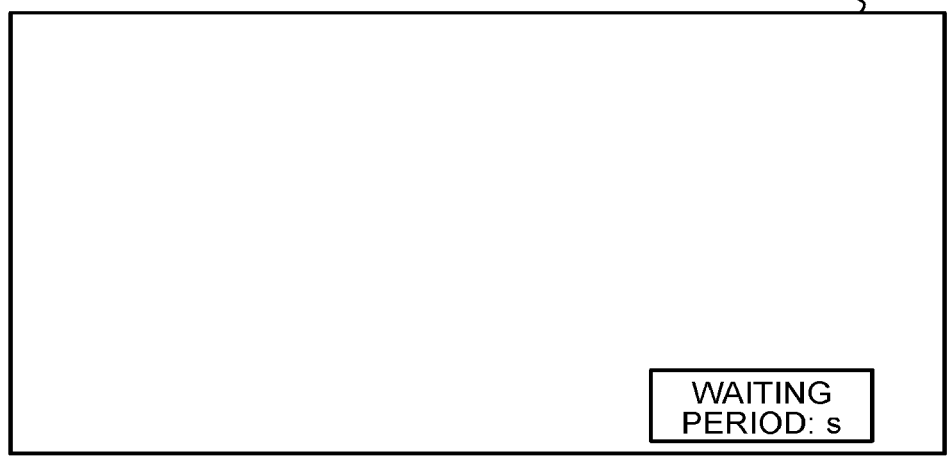

| COUNT RATE | HEAT GENERATION AMOUNT | AMBIENT TEMPERATURE | TEMPERATURE CHANGE |
|---|---|---|---|
| C<C1 | Q1 | T<T10 | T20 |
| | | T10≤T<T11 | T21 |
| | | T11≤T<T12 | T22 |
| | | T12≤T | T23 |

FIG.12

| TIME | AMBIENT TEMPERATURE | TEMPERATURE CHANGE |
|---|---|---|
| t1 | T<T10 | -T30 |
| | T10≤T<T11 | -T31 |
| | T11≤T<T12 | -T32 |
| | T12≤T | -T33 |

X-RAY CT APPARATUS AND STORAGE MEDIUM

CROSS-REFERENCE TO RELATED APPLICATIONS

This application is based upon and claims the benefit of priority from Japanese Patent Application No. 2020-023087, filed on Feb. 14, 2020; the entire contents of which are incorporated herein by reference.

FIELD

Embodiments described herein relate generally to an X-ray Computed Tomography (CT) apparatus and a storage medium.

BACKGROUND

When a photon counting detector is configured as an area detector, Application Specific Integrated Circuits (ASICs) are arranged in high density in the very vicinity of the photon counting detector, to measure a small output current from the photon counting detector. The ASICs generate heat in accordance with a count rate while acquiring a counting result.

BRIEF DESCRIPTION OF THE DRAWINGS

FIG. 4 is a chart for explaining an example of a process of obtaining initial temperature information performed by a controlling function according to the first embodiment;

FIG. 5 is a table illustrating an example of correspondence information according to the first embodiment;

FIG. 8 is a drawing illustrating an example of a distribution of incident radiation amounts according to the first embodiment;

FIG. 9 is a drawing illustrating an example of displaying a waiting period according to the first embodiment;

FIG. 12 is a table illustrating another example of the correspondence information according to the modification example;

DETAILED DESCRIPTION

Figure 1:
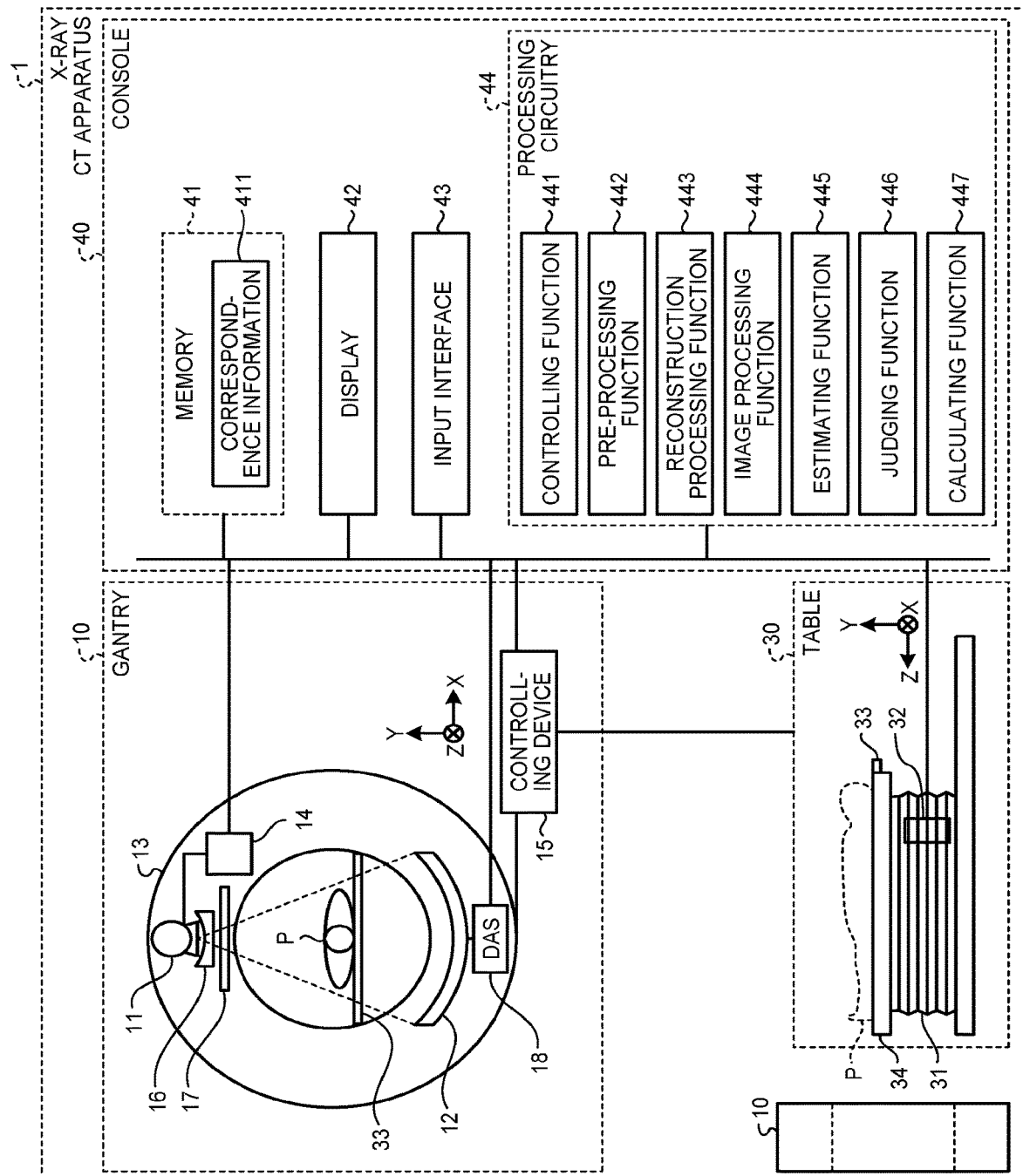
FIG. 1 is a diagram illustrating an exemplary configuration of an X-ray CT apparatus according to a first embodiment.

According to an embodiment, an X-ray CT apparatus includes processing circuitry. The processing circuitry is configured to obtain initial temperature information of a photon counting detector before a main scan, information about the shape of a subject, and a scan condition of the main scan. The processing circuitry is configured to estimate a temperature change of the photon counting detector to be observed when the main scan is performed, on the basis of the initial temperature information, the information about the shape of the subject, and information about the scan condition of the main scan. The processing circuitry is configured to judge whether or not it is possible to perform the main scan, on the basis of the temperature change and the initial temperature information.

Exemplary embodiments of an X-ray CT apparatus and a storage medium will be explained in detail below, with reference to the accompanying drawings. Possible embodiments of the X-ray CT apparatus and a storage medium of the present disclosure are not limited to the embodiments described below. Further, it is possible to combine any of the embodiments with another embodiment or a conventional technique as long as no conflict occurs. Further, in the description below, some of the constituent elements that are the same as each other will be referred to by using the same reference characters, and duplicate explanations thereof will be omitted.

Further, the X-ray CT apparatuses explained in the embodiments below are each an apparatus capable of executing a photon counting CT process. In other words, the X-ray CT apparatuses explained in the embodiments below are each an apparatus capable of reconstructing X-ray CT image data by counting X-rays that have passed through an examined subject (hereinafter "subject"), while employing an X-ray detector that uses a photon counting scheme (a photon counting detector).

First Embodiment

FIG. 1 is a diagram illustrating an exemplary configuration of an X-ray CT apparatus 1 according to a first embodiment. As illustrated in FIG. 1, the X-ray CT apparatus 1 according to the first embodiment includes a gantry 10, a table 30, and a console 40.

In FIG. 1, the rotation axis of a rotating frame 13 in a non-tilted state or the longitudinal direction of a tabletop 33 of the table 30 is defined as a Z-axis direction. Further, the axial direction orthogonal to the Z-axis direction and parallel to the floor surface is defined as an X-axis direction. The axial direction orthogonal to the Z-axis direction and perpendicular to the floor surface is defined as a Y-axis direction. Although the gantry 10 is drawn from multiple directions in FIG. 1 for the sake of convenience in the explanation, the X-ray CT apparatus 1 includes one gantry 10.

The gantry 10 includes an X-ray tube 11, an X-ray detector 12, the rotating frame 13, an X-ray high-voltage device 14, a controlling device 15, a wedge 16, a collimator 17, and a Data Acquisition System (DAS) 18.

The X-ray tube 11 is a vacuum tube having a negative pole (a filament) configured to generate thermo electrons and a positive pole (a target) configured to generate X-rays in response to collisions of the thermo electrons. The X-ray tube 11 is configured to generate X-rays to be radiated onto a subject P, by emitting the thermo electrons from the negative pole toward the positive pole, with application of high voltage from the X-ray high-voltage device 14. For example, the X-ray tube 11 may be a rotating anode X-ray tube configured to generate the X-rays by emitting the thermo electrons onto a rotating anode (positive pole).

The rotating frame 13 is an annular frame configured to support the X-ray tube 11 and the X-ray detector 12 so as to oppose each other and is configured to rotate the X-ray tube 11 and the X-ray detector 12 via the controlling device 15. For example, the rotating frame 13 is cast by using aluminum. In addition to supporting the X-ray tube 11 and the X-ray detector 12, the rotating frame 13 is also capable of further supporting the X-ray high-voltage device 14, the wedge 16, the collimator 17, the DAS 18, and the like. Further, the rotating frame 13 is also capable of further supporting other various elements that are not illustrated in FIG. 1.

The wedge 16 is a filter for adjusting the dose of the X-rays radiated from the X-ray tube 11. More specifically, the wedge 16 is a filter configured to pass and attenuate the X-rays radiated from the X-ray tube 11, so that the X-rays radiated from the X-ray tube 11 onto the subject P have a predetermined distribution. For example, the wedge 16 may be a wedge filter or a bow-tie filter and is a filter obtained by processing aluminum or the like so as to have a predetermined target angle and a predetermined thickness.

The collimator 17 is configured with lead plates or the like used for narrowing down the radiation range of the X-rays that have passed through the wedge 16 and is configured to form a slit with a combination of the plurality of lead plates or the like. The collimator 17 may be referred to as an X-ray limiter. Although FIG. 1 illustrates an example in which the wedge 16 is disposed between the X-ray tube 11 and the collimator 17, the collimator 17 may be disposed between the X-ray tube 11 and the wedge 16. In that situation, the wedge 16 is configured to pass and attenuate the X-rays which are radiated from the X-ray tube 11 and of which the radiation range has been limited by the collimator 17.

The X-ray high-voltage device 14 includes: a high-voltage generating device including electrical circuits such as a transformer, a rectifier, and the like and being configured to generate the high voltage to be applied to the X-ray tube 11; and an X-ray controlling device configured to control the output voltage in accordance with the X-rays to be generated by the X-ray tube 11. The high-voltage generating device may be of a transformer type or of an inverter type. Further, the X-ray high-voltage device 14 may be provided on the rotating frame 13 or may be provided on a fixed frame (not illustrated).

The controlling device 15 includes: processing circuitry having a Central Processing Unit (CPU) or the like; and a driving mechanism configured with a motor and an actuator or the like. Upon receipt of an input signal from an input interface 43, the controlling device 15 is configured to control operations of the gantry 10 and the table 30. Further, for example, the controlling device 15 is configured to control the rotating of the rotating frame 13, tilting of the gantry 10, operations of the table 30 and the tabletop 33, and the like. In one example, as the control to tilt the gantry 10, the controlling device 15 is configured to rotate the rotating frame 13 on an axis parallel to the X-axis direction, on the basis of tilting angle (tilt angle) information input thereto. The controlling device 15 may be provided for the gantry 10 or for the console 40.

The X-ray detector 12 is a photon counting detector and is configured, every time an X-ray photon becomes incident thereto, to output a signal that makes it possible to measure an energy value of the X-ray photon. The X-ray photon may be, for example, an X-ray photon that is radiated from the X-ray tube 11 and has passed through the subject P. The X-ray detector 12 includes a plurality of detecting elements each of which is configured to output an electrical signal (an analog signal) corresponding to one pulse every time an X-ray photon becomes incident thereto. By counting the number of electrical signals (the pulses), it is possible to count the number of X-ray photons that have become incident to the detecting elements. Further, by performing a calculation process for processing the signals, it is possible to measure the energy value of the X-ray photons that caused the output of the signals. For example, the X-ray detector 12 is an area detector in which detecting elements are arranged in N rows in a channel direction (the X-axis direction in FIG. 1) and in M rows in a slice direction (the Z-axis direction in FIG. 1).

For example, each of the detecting elements is configured by using a scintillator and an optical sensor such as a photomultiplier tube. In that situation, the X-ray detector 12 is a detector of an indirect conversion type configured to convert the incident X-ray photons into scintillator light via the scintillators and to further convert the scintillator light into the electrical signals via the optical sensors such as the photomultiplier tubes. Alternatively, in each of the detecting elements, for example, an electrode may be arranged with a semiconductor detecting element using cadmium telluride (CdTe) or cadmium zinc telluride (CdZnTe). In that situation, the X-ray detector 12 is a detector of a direct conversion type configured to directly convert the incident X-ray photons into the electrical signals.

The X-ray detector 12 includes the detecting elements and a plurality of Application Specific Integrated Circuits (ASICs) connected to the detecting elements and configured to count the X-ray photons detected by the detecting elements. The ASICs are configured to count the number of X-ray photons that have become incident to the detecting elements, by discriminating individual electric charges output by the detecting elements. Further, the ASICs are configured to measure the energy of the counted X-ray photons, by performing a calculating process based on the magnitudes of the individual electric charges. Further, the ASICs are configured to output a counting result of the X-ray photons to the DAS 18 as digital data.

Figure 2:
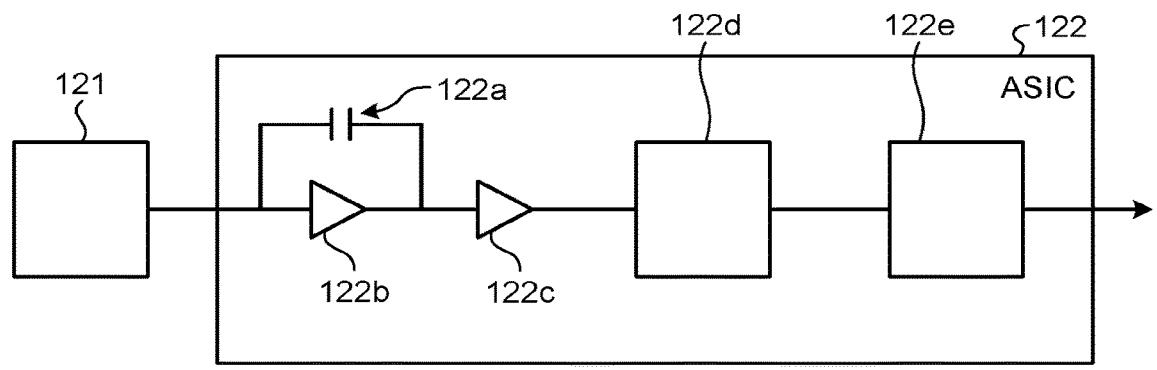
FIG. 2 is a diagram illustrating an exemplary configuration of an X-ray detector 12 according to the first embodiment.

FIG. 2 is a diagram illustrating an exemplary configuration of the X-ray detector 12 according to the first embodiment. For example, as illustrated in FIG. 2, in the X-ray detector 12, an ASIC 122 is connected to a detecting element 121. For example, an ASIC 122 includes a capacitor 122a, an amplifying circuit 122b, a waveform shaping circuit 122c, a comparator circuit 122d, and a counter 122e. Although FIG. 2 illustrates the one detecting element 121 and the one ASIC 122 for the sake of convenience in the explanation, the X-ray detector 12 includes a plurality of detecting elements 121 and a plurality of ASICs 122 in actuality.

The capacitor 122a is configured to accumulate the electric charges output by the detecting element 121. The amplifying circuit 122b is a circuit configured to integrate the electric charges collected by a capacitor 125a and to output the result as a pulse signal indicating an electrical quantity. The pulse signal has a wave height and an area corresponding to the amount of energy of the X-ray photons. In other words, the wave height value of the electrical signal (pulse) is correlated with the energy value of the X-ray photons.

The waveform shaping circuit 122c is a circuit configured to adjust frequency characteristics of the pulse signal output from the amplifying circuit 122b and to shape the waveform of the pulse signal by applying a gain and an offset thereto.

The comparator circuit 122d is a circuit configured to compare the wave height or the area of the pulse signal based on the incident X-ray photons with a threshold value being set in advance in correspondence with a plurality of energy bands to be discriminated and to output a result of the comparison with the threshold value to the counter 122e provided on the subsequent stage. More specifically, the comparator circuit 122d is configured to compare the wave height or the area of the pulse signal input thereto from the waveform shaping circuit 122c with the threshold value and, in accordance with the comparison result, to output the result to the counter 122e of a corresponding energy band.

By counting the pulse signals in each of the corresponding energy bands, the counter 122e is configured to count the X-ray photons in each energy band and to output the counting result to the DAS 18 as digital data. More specifically, in response to the input from the comparator circuit 122d, the counter 122e is configured to add up the count values corresponding to the energy bands and to output the counting result to the DAS 18.

The DAS 18 is configured to generate detection data on the basis of the results of the counting process input thereto from the X-ray detector 12. The detection data may be a sinogram, for example. The sinogram is data in which the results of the counting process indicating the incidence to the detecting elements are arranged in correspondence with different positions in the X-ray tube 11. The sinogram is data in which the results of the counting process are arranged in a two-dimensional Cartesian coordinate system of which the axes extend in a view direction and the channel direction. For example, the DAS 18 is configured to generate the sinogram in units of the rows in the slice direction within the X-ray detector 12. In this situation, the results of the counting process are represented by data in which the number of X-ray photons is assigned to each energy bin. For example, the DAS 18 is configured to count the photons (the X-ray photons) derived from the X-rays that are radiated from the X-ray tube 11 and have passed through the subject P and to obtain the results of the counting process by discriminating the energy levels of the counted X-ray photons. The DAS 18 is configured to transfer the generated detection data to the console 40. The DAS 18 is realized by using a processor, for example.

The data generated by the DAS 18 is transmitted from a transmitter including a Light Emitting Diode (LED) and being provided on the rotating frame 13, to a receiver including a photodiode and being provided in a non-rotation part (e.g., a fixed frame, which is not illustrated in FIG. 1) of the gantry 10, through optical communication, and is further transferred to the console 40. In the present example, the non-rotation part is the fixed frame or the like configured to rotatably support the rotating frame 13. The method for transmitting the data from the rotating frame 13 to the non-rotation part of the gantry 10 is not limited to optical communication and may be realized with any other contactless data transfer method or with a contact-type data transfer method.

The table 30 is a device on which the subject P to be imaged is placed and which is configured to move the subject P. The table 30 includes a base 31, a table driving device 32, the tabletop 33, and a supporting frame 34. The base 31 is a casing configured to support the supporting frame 34 so as to be movable in the vertical directions. The table driving device 32 is a driving mechanism configured to move the tabletop 33 on which the subject P is placed, along the long axis directions of the tabletop 33 and includes a motor and an actuator or the like. The tabletop 33 provided on the top face of the supporting frame 34 is a board on which the subject P is placed. In addition to the tabletop 33, the table driving device 32 may also move the supporting frame 34 along the long axis directions of the tabletop 33.

The console 40 includes a memory 41, a display 42, the input interface 43, and processing circuitry 44. In the present example, the console 40 and the gantry 10 are separate from each other; however, another arrangement is also acceptable in which the gantry 10 includes the console 40 or one or more of the constituent elements of the console 40.

The memory 41 is realized by using, for example, a semiconductor memory element such as a Random Access Memory (RAM) or a flash memory, or a hard disk, an optical disk, or the like. For example, the memory 41 is configured to store therein projection data and CT image data. Further, for example, the memory 41 has stored therein programs used by circuits included in the X-ray CT apparatus 1 for realizing the functions thereof. Further, for example, the memory 41 has stored therein correspondence information 411, as illustrated in FIG. 1. The correspondence information 411 will be explained in detail later. Alternatively, the memory 41 may be realized by using a group of servers (a cloud) connected to the X-ray CT apparatus 1 via a network.

The display 42 is configured to display various types of information. For example, the display 42 is configured to display various types of images generated by the processing circuitry 44 and to display a Graphical User Interface (GUI) used for receiving various types of operations from an operator. Further, the display 42 is configured to display information about a waiting period for a scan, and the like. The information about the waiting period for the scan will be explained in detail later. For example, the display 42 is a liquid crystal display or a Cathode Ray Tube (CRT) display. Alternatively, the display 42 may be of a desktop type or may be configured by using a tablet terminal or the like capable of wirelessly communicating with the main body of the console 40. The display 42 is an example of the display unit.

The input interface 43 is configured to receive various types of input operations from the operator, to convert the received input operations into electrical signals, and to output the electrical signals to the processing circuitry 44. Further, for example, the input interface 43 is configured to receive, from the operator, operations to input a scan condition, a reconstruction condition used at the time of reconstructing the CT image data, an image processing condition used at the time of generating a post-processing image from the CT image data, and the like.

For example, the input interface 43 is realized by using a mouse, a keyboard, a trackball, a switch, a button, a joystick, a touchpad on which input operations are performed by touching an operation surface thereof, a touch screen in which a display screen and a touchpad are integrally formed, a contactless input circuit using an optical sensor, an audio input circuit, and/or the like. Alternatively, the input interface 43 may be provided for the gantry 10. Further, the input interface 43 may be configured by using a tablet terminal or the like capable of wirelessly communicating with the main body of the console 40. Furthermore, the input interface 43 does not necessarily have to include one or more physical operation component parts such as a mouse and/or a keyboard. For instance, possible examples of the input interface 43 include an electrical signal processing circuit configured to receive an electrical signal corresponding to an input operation from an external input device provided separately from the console 40 and to output the electrical signal to the processing circuitry 44.

The processing circuitry 44 is configured to control operations of the entirety of the X-ray CT apparatus 1. For example, the processing circuitry 44 executes a controlling function 441, a pre-processing function 442, a reconstruction processing function 443, an image processing function 444, an estimating function 445, a judging function 446, and a calculating function 447. In this situation, for example, processing functions executed by the constituent elements of the processing circuitry 44 illustrated in FIG. 1, namely, the controlling function 441, the pre-processing function 442, the reconstruction processing function 443, the image processing function 444, the estimating function 445, the judging function 446, and the calculating function 447, are recorded in the memory 41 in the form of computer-executable programs. For example, the processing circuitry 44 is a processor and, by reading and executing the programs from the memory 41, is configured to realize the functions corresponding to the read programs. In other words, the processing circuitry 44 that has read the programs has the functions illustrated within the processing circuitry 44 in FIG. 1.

Although FIG. 1 illustrates the example in which the processing functions of the controlling function 441, the pre-processing function 442, the reconstruction processing function 443, the image processing function 444, the estimating function 445, the judging function 446, and the calculating function 447 are realized by the single processing circuit (i.e., the processing circuitry 44), possible embodiments are not limited to this example. For instance, it is also acceptable to structure the processing circuitry 44 by combining together a plurality of independent processors, so that the processing functions are realized as a result of the processors executing the programs. Further, the processing functions of the processing circuitry 44 may be realized as being distributed among, or integrated together in, one or more processing circuits, as appropriate.

The controlling function 441 is configured to control various types of processes on the basis of input operations received from the operator via the input interface 43. More specifically, the controlling function 441 is configured to control a CT scan performed by the gantry 10. For example, the controlling function 441 is configured to control the counting result acquiring process performed by the gantry 10, by controlling operations of the X-ray high-voltage device 14, the X-ray detector 12, the controlling device 15, the DAS 18, and the table driving device 32. In one example, the controlling function 441 is configured to control a position determining scan to acquire a position determining image (a scanogram image) and a projection data acquiring process in an imaging process (a main scan) to acquire one or more images used for a diagnosis purpose.

Further, the controlling function 441 is configured to control obtaining various types of information. The information obtained by the controlling function 441 will be explained in detail later. Further, the controlling function 441 is configured to exercise control so that the display 42 displays any of the various types of image data stored in the memory 41 and the information about the waiting period for the scan.

The pre-processing function 442 is configured to generate projection data by performing pre-processing processes such as a logarithmic conversion process, an offset correcting process, an inter-channel sensitivity correcting process, a beam hardening correction, and/or the like, on the detection data output from the DAS 18.

The reconstruction processing function 443 is configured to generate the CT image data by performing a reconstructing process using a filtered back projection method, a successive approximation reconstruction method, or the like, on the projection data generated by the pre-processing function 442. The reconstruction processing function 443 is configured to store the reconstructed CT image data into the memory 41.

In this situation, the projection data generated from the counting result obtained in the photon counting CT process includes information about the energy of the X-rays attenuated as a result of passing through the subject P. For this reason, the reconstruction processing function 443 is capable of reconstructing CT image data corresponding to a specific energy component, for example. Further, the reconstruction processing function 443 is also capable of reconstructing CT image data corresponding to each of a plurality of energy components, for example.

Further, for example, the reconstruction processing function 443 is also capable of assigning a tone corresponding to an energy component to each of the pixels in the CT image data representing the energy components and thus generating image data in which a plurality of pieces of CT image data color-coded according to the energy components are superimposed on one another. Further, the reconstruction processing function 443 is capable, for example, of generating image data that makes it possible to identify a substance by using a K-absorption edge unique to the substance. Other examples of image data generated by the reconstruction processing function 443 include monochrome X-ray image data, density image data, and effective atomic number image data.

To reconstruct the CT image data, it is necessary to have projection data corresponding to 360° of the entire circumference around the subject or, when a half scan method is used, projection data corresponding to "180°+a fan angle". Both of these reconstruction methods are applicable to the present embodiment.

On the basis of an input operation received from the operator via the input interface 43, the image processing function 444 is configured convert the CT image data generated by the reconstruction processing function 443 into image data of a tomographic image taken on an arbitrary cross-sectional plane or a three-dimensional image or the like resulting from a rendering process, by using a publicly-known method. The image processing function 444 is configured to store the image data resulting from the conversion, into the memory 41.

The estimating function 445 is configured to estimate a temperature change of the X-ray detector 12. The judging function 446 is configured to judge whether or not it is possible to execute the main scan, on the basis of the temperature change of the X-ray detector 12. The calculating function 447 is configured to calculate a waiting period for the scan. Processes performed by the various types of functions will be explained in detail later. The estimating function 445 is an example of the estimating unit. The judging function 446 is an example of the judging unit. The calculating function 447 is an example of the calculating unit.

A configuration of the X-ray CT apparatus 1 according to the first embodiment has thus been explained. The X-ray CT apparatus 1 structured as described above makes it possible to efficiently proceed with the scan using the photon counting detector. As explained above, in the photon counting detector, the ASICs generate heat in a heat generation amount corresponding to the incident radiation amount of the X-rays. In this regard, because a rise in the temperature of the detector caused by the heat generation of the ASICs has an impact on performance of the detector, it is necessary to manage the temperature of the detector so as not to reach such a temperature (an upper limit temperature) that impacts the performance thereof.

For this reason, the X-ray CT apparatus 1 according to the present embodiment makes it possible to efficiently proceed with the scan, by estimating a temperature change of the X-ray detector 12 and further judging whether or not it is possible to perform the scan on the basis of the estimated temperature change. More specifically, the X-ray CT apparatus 1 is configured to judge whether or not it is possible to perform the scan, by obtaining information about an initial temperature, which is the temperature of the X-ray detector 12 before the scan is started, estimating a temperature of the X-ray detector 12 that will be reached when the scan is performed under a scan condition being set, and judging whether or not the estimated temperature exceeds the upper limit temperature.

Figure 3:
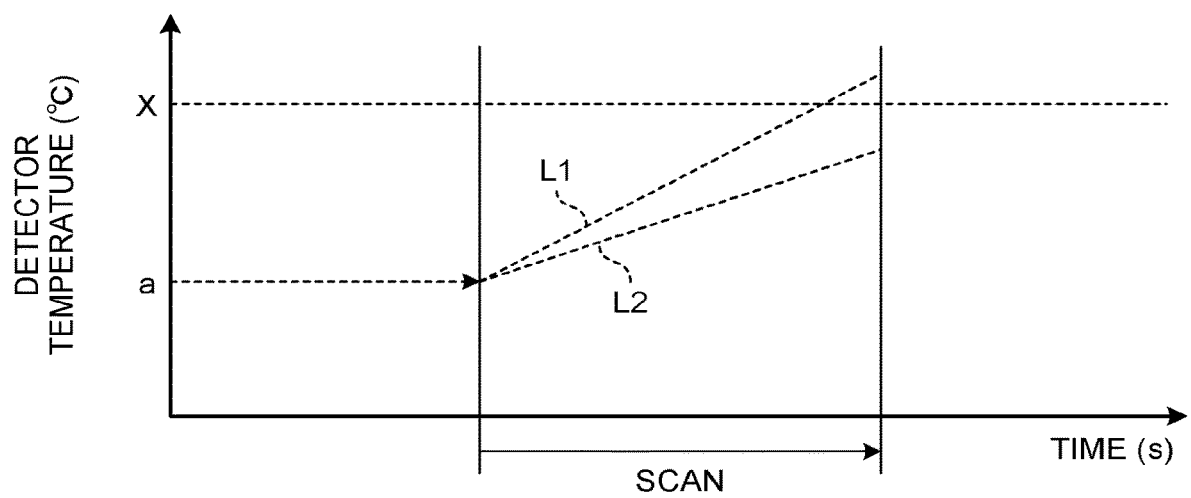
FIG. 3 is a chart for explaining an outline of a process performed by the X-ray CT apparatus according to the first embodiment.

FIG. 3 is a chart for explaining an outline of a process performed by the X-ray CT apparatus 1 according to the first embodiment. FIG. 3 presents a graph of temperature changes in which the vertical axis expresses "detector temperature (° C.)", whereas the horizontal axis expresses "time (s)". For example, the X-ray CT apparatus 1 obtains information about an initial temperature "a" of the detector at the starting time of the scan. Further, on the basis of the scan condition, the X-ray CT apparatus 1 estimates an amount of heat generated by the X-ray detector 12 (hereinafter, "heat generation amount") and estimates the temperature change from the initial temperature "a".

In this situation, for example, when the estimated temperature change is indicated by a straight line L1 in FIG. 3, the X-ray CT apparatus 1 determines that it is impossible to perform the scan, because the post-change temperature would exceed the upper limit temperature "X". On the contrary, when the estimated temperature is indicated by the straight line L2 in FIG. 3, the X-ray CT apparatus 1 determines that it is possible to perform the scan, because the post-change temperature will not exceed the upper limit temperature "X".

As explained above, the heat generation amount of the ASICs vary depending on the incident radiation amount of the X-rays. Accordingly, the X-ray CT apparatus 1 exercises control so that the entirety of the X-ray detector 12 does not exceed the upper limit temperature, by judging whether or not the post-change temperature exceeds the upper limit temperature in such a position where the heat generation amount is largest in the X-ray detector 12. In the following sections, details of the process performed by the X-ray CT apparatus 1 will be explained.

The controlling function 441 according to the present embodiment is configured to obtain the initial temperature information of the X-ray detector 12 (the photon counting detector) before the main scan, information about the shape of the subject, and the scan condition of the main scan. In this situation, the controlling function 441 is able to obtain the initial temperature information on the basis of a count rate of the X-ray detector 12 during a position determining scan or a temperature sensor. In the following sections, at first, a process performed by the X-ray CT apparatus 1 when the count rate during the position determining scan is used will be explained.

In that situation, the controlling function 441 calculates a heat generation amount on the basis of the number of incident photons per unit time period (the count rate) measured by performing the position determining scan and obtains temperature information of the X-ray detector 12 at present on the basis of the calculated heat generation amount. FIG. 4 is a chart for explaining an example of the process of obtaining the initial temperature information performed by the controlling function 441 according to the first embodiment. FIG. 4 illustrates a graph of temperature changes in which the vertical axis expresses "detector temperature (° C.)", whereas the horizontal axis expresses "time (s)".

For example, the controlling function 441 obtains information about a count rate in each of the acquisition positions during the position determining scan and further calculates a heat generation amount in the position having the highest count rate. After that, the controlling function 441 obtains the temperature (the temperature "a" in FIG. 4) of the X-ray detector 12 at present (after the position determining scan), by taking a temperature change based on the heat generation amount into account, with the temperature (the temperature "b" in FIG. 4) of the X-ray detector 12 before the position determining scan.

In this situation, as the correspondence information 411, the X-ray CT apparatus 1 has stored in the memory 41, in advance, heat generation amounts corresponding to count rates and information about temperature changes corresponding to the heat generation amounts. FIG. 5 is a table illustrating an example of the correspondence information 411 according to the first embodiment. For example, as illustrated in FIG. 5, the memory 41 has stored therein the correspondence information in which count rates, heat generation amounts, and temperature changes are kept in correspondence with one another.

In one example, the memory 41 has stored therein correspondence information indicating "count rate: C<C1; heat generation amount: Q1; temperature change: Tl". This correspondence information indicates that when the count rate "C" is lower than "C1", the heat generation amount is "Q1" and that when the heat generation amount is "Q1", the temperature change is "Tl". Similarly, the memory 41 has stored therein correspondence information in which a heat generation amount and a temperature change are kept in correspondence with each other, for the situation where the count rate "C" is "C1" or higher but is lower than "C2", the situation where the count rate "C" is "C2" or higher but is lower than "C3", and the situation where the count rate "C"

is "C3" or higher. In this situation, the heat generation amounts corresponding to the count rates can each be calculated by using an expression "the heat generation amount (Q)=voltage (V)×current (A)×count×k (count)". Accordingly, for example, the memory 41 may store therein the correspondence information illustrated in FIG. 5 for each of various scan conditions (voltage and current values).

The example in FIG. 5 is for an illustration purpose only, and possible embodiments of the correspondence information keeping count rates, heat generation amounts, and temperature changes in correspondence with one another are not limited to this example. For instance, as the correspondence information, it is also possible to store the expression presented above used for calculating a heat generation amount corresponding to a count rate and the correspondence relationship between heat generation amounts and temperature changes. In that situation, the controlling function 441 calculates a heat generation amount by using the expression presented above and obtains a temperature change corresponding to the calculated heat generation amount.

The controlling function 441 obtains information about the count rate in each of the acquisition positions during the position determining scan and further calculates the temperature change corresponding to the highest count rate on the basis of the correspondence information illustrated in FIG. 5. After that, the controlling function 441 obtains the initial temperature "a", by taking the calculated temperature change into account, with the temperature (the temperature "b" in FIG. 4) before the position determining scan.

In this situation, the temperature "b" of the X-ray detector 12 before the position determining scan may be a pre-set temperature or a temperature estimated on the basis of the most recent scan. For example, when a certain time period has elapsed since the execution of the scan, the pre-set temperature is used as the temperature "b". In other words, when the temperature of the X-ray detector 12 has not been increased by generated heat, the pre-set temperature is used as the temperature "b" corresponding to before the position determining scan. In this situation, the pre-set temperature may be the temperature of the X-ray detector 12 directly measured while no heat is generated or may be a temperature based on the room temperature of the examination room in which the X-ray CT apparatus 1 is installed.

Further, for example, when the certain time period has not elapsed since the execution of the scan, a temperature estimated on the basis of the most recent scan is used as the temperature "b". In other words, on the basis of the elapsed time period since the end of the most recent scan, the controlling function 441 calculates the temperature of the X-ray detector 12 at present and uses the calculated temperature as the temperature "b".

Figures 6, 7:
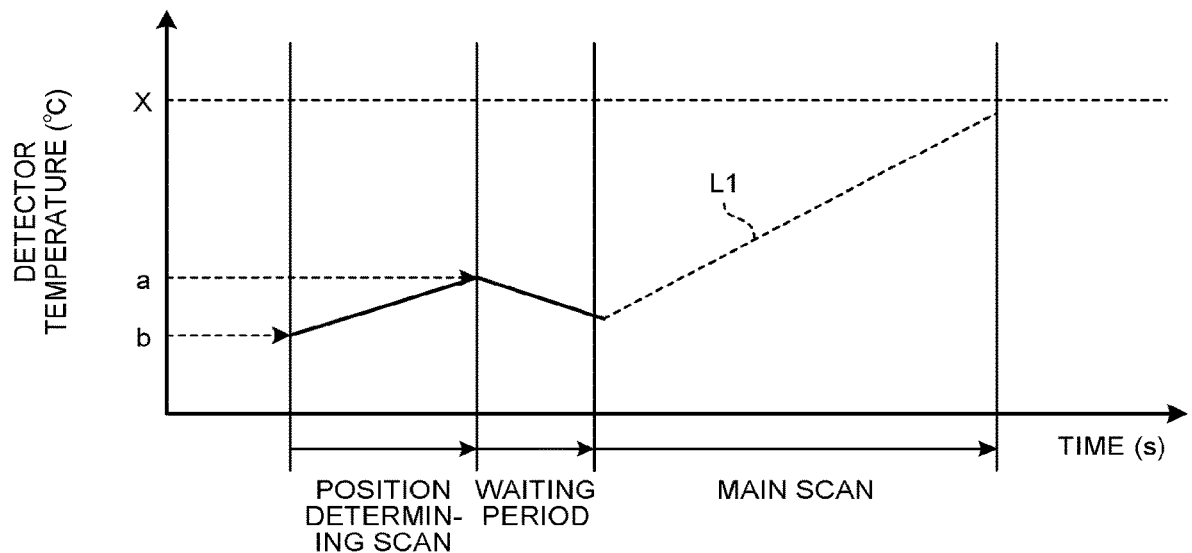
FIG. 6 is a table illustrating another example of the correspondence information according to the first embodiment.
FIG. 7 is a chart for explaining an example of a process performed by a calculating function according to the first embodiment.

In this situation, a correspondence relationship between elapsed time periods and temperature changes while no scan is being performed is stored in the memory 41 as the correspondence information 411. FIG. 6 is a table illustrating another example of the correspondence information 411 according to the first embodiment. As illustrated in FIG. 6, for example, the memory 41 stores therein the correspondence information keeping time periods and temperature changes in correspondence with each other.

In one example, the memory 41 has stored therein correspondence information indicating "time period: t1; temperature change: −T5". This correspondence information indicates that when the elapsed time period is "t1", the temperature change is "−T5". Similarly, the memory 41 has stored therein correspondence information keeping a temperature change in correspondence with each of various elapsed time periods. The example in FIG. 6 is for an illustration purpose only, and possible embodiments of the correspondence information keeping time periods in correspondence with temperature changes are not limited to this example. For instance, the memory 41 may store therein a relational expression indicating a relationship between elapsed time periods and temperature changes.

The controlling function 441 is configured to obtain the temperature of the X-ray detector 12 immediately after the most recent scan. After that, by referring to the correspondence information illustrated in FIG. 6, the controlling function 441 is configured to calculate a temperature change corresponding to the elapsed time period since the end of the most recent scan and to further calculate the temperature of the X-ray detector 12 at present, by taking the calculated temperature change into account, with the temperature of the X-ray detector 12 immediately after the most recent scan.

The controlling function 441 is configured to obtain the initial temperature "a" and to also obtain subject information and the scan condition, so as to transmit the obtained information to the estimating function 445. For example, on the basis of a position determining image obtained by performing the position determining scan, the controlling function 441 obtains the information about the shape of the subject including the body thickness of the subject or the like. Further, the controlling function 441 is configured to obtain the scan condition of the main scan performed on the subject.

In this situation, the information about the shape of the subject does not necessarily have to be based on the position determining image obtained by performing the position determining scan and may be obtained by using any of other various methods. For example, the information about the shape of the subject may be obtained on the basis of an optical image taken by an optical camera or may be obtained by estimating a physique on the basis of physique information (height, weight, and the like) of the subject.

For example, when the information about the shape of the subject is obtained on the basis of an optical image, the X-ray CT apparatus 1 is connected to an optical camera, so as to obtain an optical image of the subject taken by the optical camera. Further, on the basis of the optical image of the subject, the controlling function 441 is configured to obtain the information about the shape of the subject including the body thickness of the subject or the like. In one example, the controlling function 441 is configured to extract the subject rendered in the optical image and to obtain the information about the shape of the subject rendered in the optical image, on the basis of a correspondence relationship between sizes rendered in optical images and the actual sizes.

Further, for example, when obtaining the shape information on the basis of the physique information of the subject, the controlling function 441 is configured to obtain the physique information of the subject via a network. After that, the controlling function 441 is configured to obtain the information about the shape, by estimating the shape of a scanned site, on the basis of the obtained physique information.

On the basis of the initial temperature information, the information about the shape of the subject, and the information about the scan condition of the main scan, the estimating function 445 is configured to estimate the temperature change of the X-ray detector 12 to be observed when the main scan is performed. More specifically, on the basis of the information about the shape of the subject and the information about the scan condition of the main scan, the estimating function 445 is configured to estimate a heat generation amount of the X-ray detector 12 to be observed when the main scan is performed and to further estimate the temperature change on the basis of the initial temperature information and the heat generation amount. In other words, the estimating function 445 is configured to estimate the temperature of the X-ray detector 12 to be observed when the main scan is performed, on the basis of the initial temperature information and a temperature increase value based on the heat generation amount.

For example, the estimating function 445 is configured to estimate a count rate to be observed when the main scan is performed, on the basis of subject information and the scan condition of the main scan. For example, the estimating function 445 is configured to estimate a count rate corresponding to each of different positions to be observed when the main scan is performed, on the basis of the subject information such as the body thickness of the subject and the imaged site and the scan condition such as an X-ray tube voltage and an X-ray tube current.

After that, by referring to the correspondence information illustrated in FIG. 5, the estimating function 445 is configured to estimate a heat generation amount corresponding to the estimated count rate in each of the different positions and to further estimate a temperature change in each of the positions on the basis of the estimated heat generation amount. For example, the estimating function 445 estimates a temperature increase value in each of the different positions in the X-ray detector 12 on the basis of the estimated heat generation amounts. Subsequently, the estimating function 445 is configured to transmit the information about the estimated temperature change in each of the positions, to the judging function 446.

On the basis of the temperature changes, the judging function 446 is configured to judge whether or not it is possible to perform the main scan at the time of obtaining the initial temperature information. More specifically, the judging function 446 is configured to compare the post-change temperature of the X-ray detector 12 with a threshold value, and when the post-change temperature does not exceed the threshold value, to determine that the main scan is to be performed. For example, the judging function 446 judges whether or not the temperature of the X-ray detector 12 will exceed the upper limit temperature when the main scan is performed, by taking the temperature changes estimated by the estimating function 445 into account, with the initial temperature observed at the end of the position determining scan. In other words, the judging function 446 judges whether or not the upper limit temperature "X" will be exceeded, when the temperature increase value estimated by the estimating function 445 is added to the initial temperature (the temperature "a") observed at the end of the position determining scan illustrated in FIG. 4.

In this situation, when the upper limit temperature "X" would be exceeded (the example with the straight line L1 in FIG. 4), the judging function 446 determines that it is impossible to perform the main scan. On the contrary, when the upper limit temperature "X" will not be exceeded (the example with the straight line L2 in FIG. 4), the judging function 446 determines that it is possible to perform the main scan.

When the judging function 446 has determined that it is possible to perform the main scan, the controlling function 441 controls the execution of the main scan after the position determining scan, in response to an operation performed by the operator to start the main scan.

On the contrary, when the judging function 446 has determined that it is impossible to perform the main scan, the calculating function 447 is configured to calculate a waiting period until it becomes possible to perform the main scan. In other words, when the judgment result of the judging function 446 indicates that it is impossible to perform the main scan at the time immediately after the position determining scan, the calculating function 447 is configured to calculate the waiting period until the X-ray detector 12 reaches a temperature at which it is possible to perform the main scan.

FIG. 7 is a chart for explaining an example of a process performed by the calculating function 447 according to the first embodiment. FIG. 7 illustrates a graph of temperature changes in which the vertical axis expresses "detector temperature (° C.)", whereas the horizontal axis expresses "time (s)". For example, when the judgment result of the judging function 446 is indicated by the straight line L1 in FIG. 4, the calculating function 447 calculates a waiting period until the temperature of the X-ray detector 12 no longer exceeds the upper limit temperature "X", even with the temperature change estimated by the estimating function 445 taken into account.

In other words, the X-ray CT apparatus 1 according to the present embodiment is configured to let the temperature of the X-ray detector 12 fall from the initial temperature "a" by waiting without performing the main scan and to thus exercise control so that the temperature of the X-ray detector 12 no longer exceeds the upper limit temperature "X", even with the temperature change estimated by the estimating function 445 taken into account.

On the basis of the correspondence information between the time periods and the temperature changes, the calculating function 447 is configured to calculate the waiting period until the temperature falls by the amount exceeding the upper limit temperature "X", when the temperature change estimated by the estimating function 445 is taken into account with the initial temperature. For example, by using the correspondence information illustrated in FIG. 6, the calculating function 447 is configured to calculate the time period corresponding to the temperature in the amount exceeding the upper limit temperature "X".

As explained above, because the heat generation amounts of the ASICs vary depending on the incident radiation amount, the X-ray CT apparatus 1 is configured to judge whether or not the post-change temperature exceeds the upper limit temperature in such a position of the X-ray detector 12 that has the largest heat generation amount and, when the upper limit temperature would be exceeded, to further calculate the waiting period. In this situation, the distribution of radiation amounts incident to the X-ray detector 12 varies depending on the shape of the subject, exposure directions of the X-rays, and the scan condition.

FIG. 8 is a drawing illustrating an example of the distribution of the incident radiation amounts according to the first embodiment. In FIG. 8, the top section illustrates X-ray exposure directions for the subject, whereas the bottom section illustrates a distribution of incident radiation amounts observed when the subject is exposed to X-rays in the exposure directions indicated in the top section. In the bottom section of FIG. 8, the vertical axis expresses "incident radiation amounts", whereas the horizontal axis expresses the positions of the "detecting elements in the channel direction". In other words, the bottom section of FIG. 8 illustrates the distribution of the incident radiation amounts with respect to a group of detecting elements corresponding to one slice arranged in the channel direction.

For example, the distribution of the radiation amounts of the X-rays becoming incident to the X-ray detector 12 exhibits a large incident radiation amount in an interface part between the subject and the air, as illustrated in FIG. 8. The reason is that the X-rays are restricted by the wedge 16 and the collimator 17 from becoming incident to a region on the outside of the subject and that the X-rays are controlled so as to become incident to the subject while having a predetermined distribution.

For example, when the center of the subject matches the center of a Field Of View (FOV), it is considered that the incident radiation amounts caused by a series of exposures during the main scan exhibit the largest value, with the detecting element in the position at the interface part between the subject and the air at the exposure from "0°" illustrated in the top section of FIG. 8. Accordingly, when the acquisition in the position determining scan is performed only from the one direction corresponding to "0°" illustrated in the top section of FIG. 8, the X-ray CT apparatus 1 determines that the heat generation amount is highest from the ASIC corresponding to the detecting element in the position where the count rate is highest in the position determining scan and exercises control so that the temperature in that position does not exceed the upper limit temperature. In other words, the controlling function 441, the estimating function 445, the judging function 446, and the calculating function 447 perform the process described above with respect to the position having the highest count rate during the position determining scan.

When the position determining scan is performed in multiple directions, the controlling function 441 calculates an average value of the count rates corresponding to the directions and further identifies a position having the largest heat generation amount on the basis of a temperature change corresponding to the calculated average value. The estimating function 445, the judging function 446, and the calculating function 447 perform the process described above by using the identified position.

When the waiting period has been calculated by the calculating function 447 as explained above, the controlling function 441 is configured to exercise control so that the display 42 displays the calculated waiting period, as illustrated in FIG. 9. In this situation, the waiting period displayed on the display 42 may be a time period until the main scan is started or may be a time period until the main scan is finished (the time period until the main scan is started+the time period required by the main scan). When an operation to start the main scan is received after the waiting period is displayed, the controlling function 441 exercises control so that the main scan is executed after the waiting period has elapsed. FIG. 9 is a drawing illustrating the example of displaying the waiting period according to the first embodiment.

As explained above, the X-ray CT apparatus 1 is configured to judge whether or not the temperature of the X-ray detector 12 will exceed the upper limit temperature due to the scan, and when the upper limit temperature would be exceeded, to cause the waiting period to be displayed. With this arrangement, the X-ray CT apparatus 1 is able to help the operator understand the time period required by the scan with respect to each subject and thus makes it possible to efficiently proceed with the scan.

In the embodiment above, the example was explained in which the initial temperature is obtained on the basis of the count rates during the position determining scan. However, possible embodiments are not limited to this example. The initial temperature may be obtained by using a temperature sensor. In that situation, the X-ray detector 12 is provided with the temperature sensor.

Figures 10, 11:
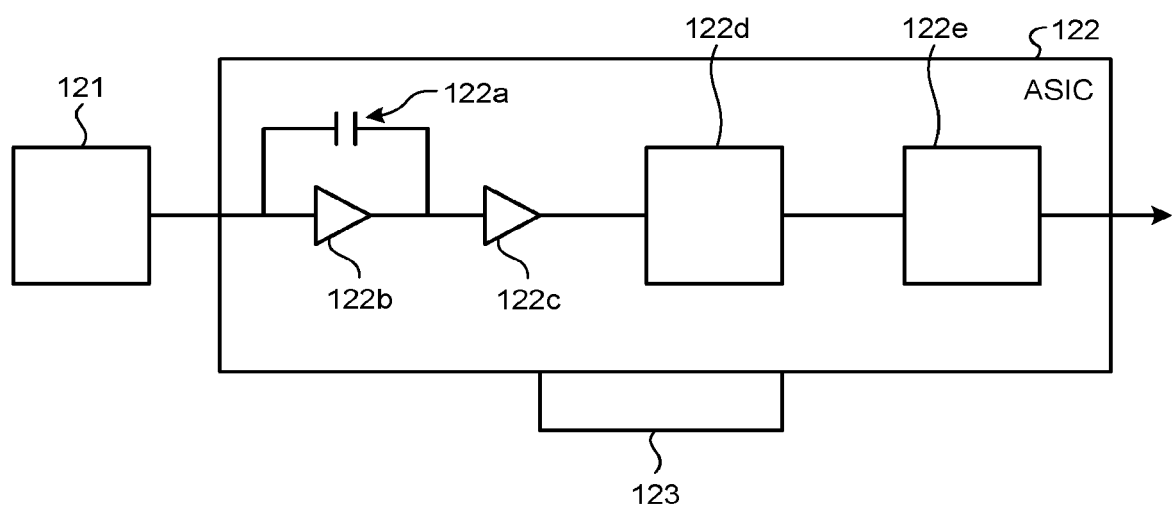
FIG. 10 is a diagram illustrating another exemplary configuration of the X-ray detector 12 according to the first embodiment.
FIG. 11 is a table illustrating an example of correspondence information according to a modification example.

FIG. 10 is a diagram illustrating another exemplary configuration of the X-ray detector 12 according to the first embodiment. For example, the X-ray detector 12 further includes a temperature sensor 123, as illustrated in FIG. 10. For example, the temperature sensor 123 may be a thermocouple, a resistance temperature detector, a thermistor, or an Integrated Circuit (IC) temperature sensor.

The controlling function 441 is configured to obtain the initial temperature information of the X-ray detector 12, by obtaining temperature information detected by the temperature sensor 123. For example, the controlling function 441 is configured to obtain a temperature detected by the temperature sensor 123 after the position determining scan is performed, as an initial temperature.

The temperature sensor 123 may be provided for each of the ASICs 122. Alternatively, temperature sensors 123 may be arranged at prescribed intervals. When the temperature sensors 123 are arranged at the prescribed intervals, the memory 41 has stored therein correspondence information indicating a correspondence relationship between temperatures detected by the temperature sensors 123 and temperatures of the ASICs 122. The controlling function 441 is configured to obtain the temperature of the ASICs 122 derived from the temperatures detected by the temperature sensors 123, on the basis of the correspondence information about the temperatures stored in the memory 41.

In this situation, the temperature sensors 123 according to the present embodiment do not necessarily have to be newly provided. For example, a temperature protecting circuit installed for the purpose of protecting circuits may be used. In that situation, the controlling function 441 obtains the initial temperature, by reading temperature information from the temperature protecting circuit.

The estimating function 445, the judging function 446, and the calculating function 447 are configured to perform the various types of processes described above, by using the initial temperature obtained on the basis of the temperature sensors 123.

Modification Examples

In the embodiment above, the example was explained in which the control is exercised on the basis of the temperature changes in the situation where impacts of ambient temperature in the surroundings of the X-ray detector 12 are not taken into consideration. In a modification example, exercising control on the basis of temperature changes while the ambient temperature is taken into consideration will be explained. In that situation, a temperature sensor (not illustrated) is provided in the surroundings of the X-ray detector 12, so that the controlling function 441 obtains information about the ambient temperature detected by the temperature sensor. Further, the controlling function 441 is configured to obtain information about an initial temperature by using the obtained ambient temperature and the count rates during the position determining scan.

In the present example, when the ambient temperature is taken into consideration, the X-ray CT apparatus 1 has stored in the memory 41, in advance, heat generation amounts corresponding to count rates and information about temperature changes corresponding to the heat generation amounts and to the ambient temperature, as the correspondence information 411. FIG. 11 is a table illustrating an example of the correspondence information 411 according to the modification example. For example, as illustrated in FIG. 11, the memory 41 has stored therein the correspondence information keeping count rates, heat generation amounts, ambient temperatures, and temperature changes, in correspondence with one another.

In an example, the memory 41 has stored therein correspondence information indicating "count rate: C<C1; heat generation amount: Q1; ambient temperature: T<T10; temperature change: T20". This correspondence information indicates that when the count rate "C" is lower than "C1", the heat generation amount is "Q1" and that when the heat generation amount is "Q1" while the ambient temperature "T" is lower than "T10", the temperature change is "T20". Similarly, the memory 41 has stored therein correspondence information in which temperature changes are kept in correspondence, for the situation where the heat generation amount is "Q1" while the ambient temperature "T" is "T10" or higher but is lower than "T11"; the situation where the heat generation amount is "Q1" while the ambient temperature "T" is "T11" or higher but is lower than "T12"; and the situation where the heat generation amount is "Q1" while the ambient temperature "T" is "T12" or higher.

Although FIG. 11 illustrates only the correspondence information for the situation where "count rate: C<C1"; heat generation amount: Q1", the memory 41 has stored therein, in actuality, temperature changes corresponding to various ambient temperatures for the situation where "count rate C1≤C<C2; heat generation amount: Q2"; the situation where "count rate C2≤C<C3; heat generation amount: Q3"; and the situation where "count rate C3≤C; heat generation amount: Q4". The examples in FIG. 11 are for an illustration purpose only, and possible embodiments of the correspondence information keeping count rates, heat generation amounts, ambient temperatures, and temperature changes in correspondence with one another are not limited to this example.

The controlling function 441 is configured to obtain information about the count rate in each of the acquisition positions during the position determining scan and to calculate a temperature change corresponding to the highest count rate, on the basis of the correspondence information illustrated in FIG. 11. Further, the controlling function 441 is configured to obtain an initial temperature by taking the calculated temperature changes into account, with the temperature before the position determining scan.

Further on the basis of the information about the ambient temperature of the X-ray detector 12, the estimating function 445 is configured to estimate a heat generation amount of the X-ray detector 12 to be observed when the main scan is performed and to further estimate a temperature change on the basis of the initial temperature information and the heat generation amounts. For example, on the basis of the subject information and the scan condition of the main scan, the estimating function 445 is configured to estimate count rates to be observed when the main scan is performed. Also, the estimating function 445 is configured to obtain the ambient temperature.

Further, by referring to the correspondence information illustrated in FIG. 11, the estimating function 445 is configured to estimate a heat generation amount corresponding to the estimated count rate in each of the positions and to further estimate a temperature change in each position on the basis of the heat generation amount and the ambient temperature. For example, on the basis of the heat generation amount and the ambient temperature, the estimating function 445 is configured to estimate a temperature increase value in each of the positions in the X-ray detector 12. After that, the estimating function 445 is configured to transmit information about the estimated temperature change in each of the positions, to the judging function 446.

The judging function 446 is configured to judge whether or not the temperature of the X-ray detector 12 will exceed the upper limit temperature when the main scan is performed, by taking the temperature changes estimated by the estimating function 445 into account, with the initial temperature observed at the end of the position determining scan.

When the judging function 446 has determined that it is impossible to perform the main scan, the calculating function 447 is configured to calculate a waiting period until the X-ray detector 12 reaches the temperature at which it is possible to perform the main scan, while taking the ambient temperature into consideration.

In this situation, when the ambient temperature is taken into consideration, the X-ray CT apparatus 1 has stored in the memory 41, in advance, information indicating a correspondence relationship among elapsed time periods, ambient temperatures, and temperature changes while no scan is being performed, as the correspondence information 411. FIG. 12 is a table illustrating another example of the correspondence information 411 according to the modification example. For instance, as illustrated in FIG. 12, the memory 41 has stored therein the correspondence information keeping time periods, ambient temperatures, and temperature changes in correspondence with one another.

In an example, the memory 41 has stored therein correspondence information indicating "time: t1; ambient temperature: T<T10; temperature change: −T30. This correspondence information indicates that when the elapsed time period is "t1", while the ambient temperature "T" is "T10" or lower, the temperature change is "−T30". Similarly, the memory 41 has stored therein correspondence information keeping a temperature change in correspondence with each of the different ambient temperatures when the elapsed time period is "t1". Although FIG. 12 illustrates only the examples with the elapsed time period "t1", the memory 41 has stored therein, in actuality, correspondence information keeping a temperature change in correspondence with each of the different ambient temperatures, with respect to each of the elapsed time periods "t2", "t3", "t4", and "t5". The example in FIG. 12 is for an illustration purpose only, and possible embodiments of the correspondence information keeping time periods, ambient temperatures, and temperature changes in correspondence with one another are not limited to this example. For instance, the memory 41 may store therein a relational expression indicating a relationship among elapsed time periods, ambient temperatures, and temperature changes.

When an ambient temperature is obtained, the controlling function 441 is able to use the correspondence information illustrated in FIG. 12 for calculating the temperature "b" of the X-ray detector 12 corresponding to before the position determining scan. In other words, when a certain time period has not elapsed since the execution of the scan, and a temperature estimated on the basis of the most recent scan is used as the temperature "b", the controlling function 441 calculates the temperature of the X-ray detector 12 at present on the basis of the correspondence information illustrated in FIG. 12. For example, on the basis of the correspondence information illustrated in FIG. 12, the controlling function 441 calculates a temperature change corresponding to the elapsed time period since the end of the most recent scan and to the ambient temperature and further calculates the temperature of the X-ray detector 12 at present by taking the calculated temperature change into account, with the temperature of the X-ray detector 12 immediately after the most recent scan.

Figure 13:
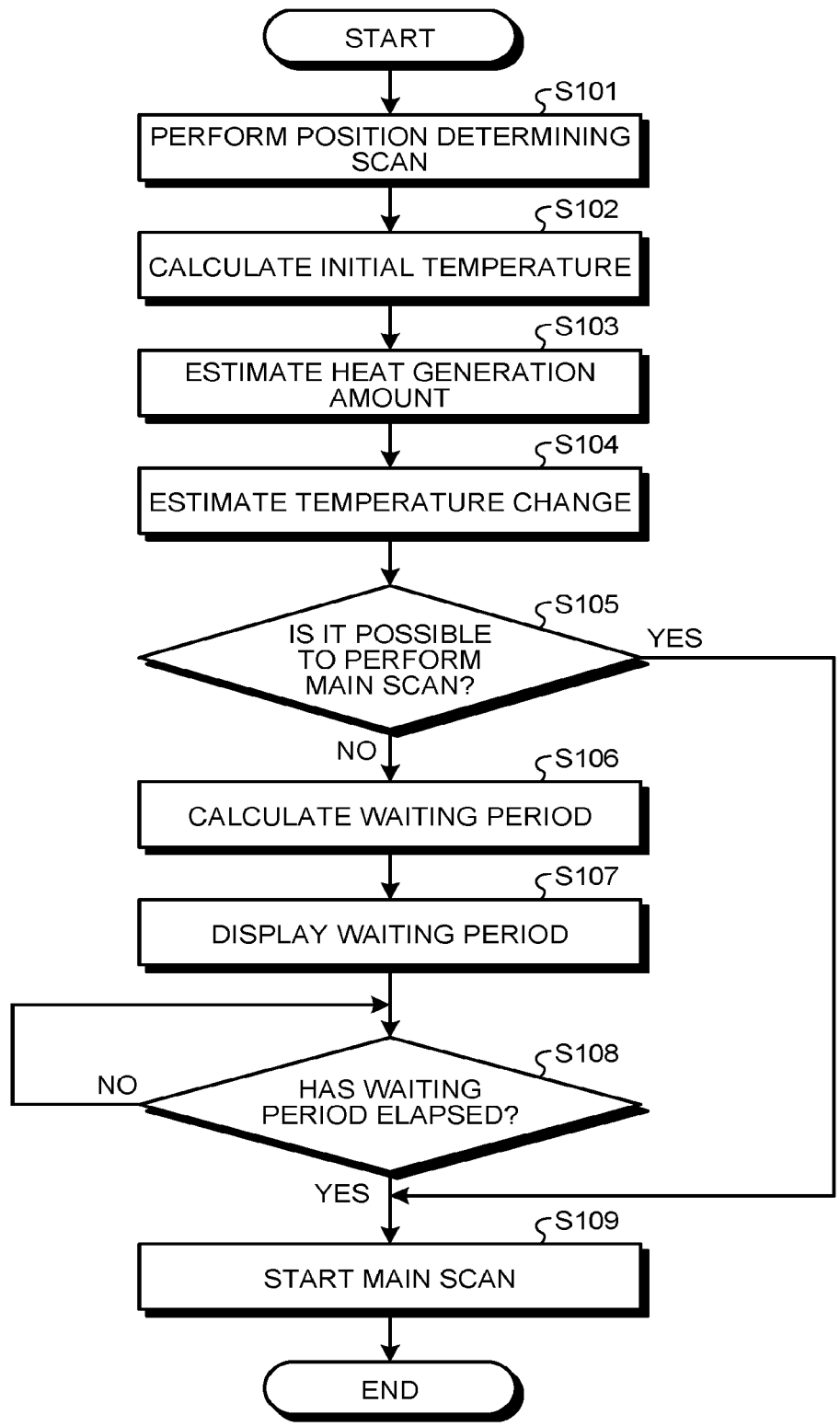
FIG. 13 is a flowchart for explaining a procedure in a process performed by the X-ray CT apparatus according to the first embodiment.
Figure 14:
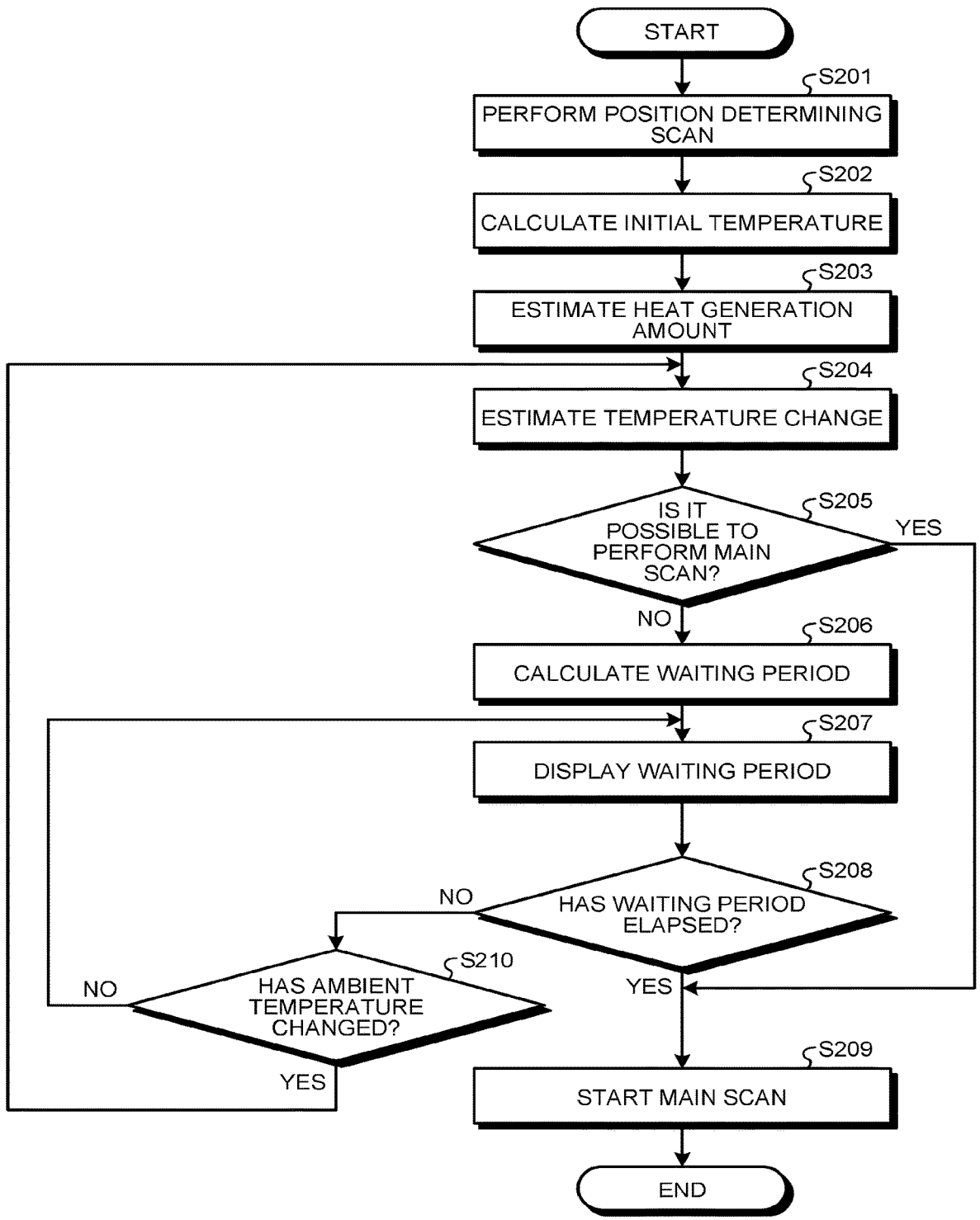
FIG. 14 is a flowchart for explaining a procedure in a process performed by an X-ray CT apparatus according to a modification example.

Next, a process performed by the X-ray CT apparatus 1 according to the first embodiment and a process performed by the X-ray CT apparatus 1 according to the modification example will be explained, with reference to FIGS. 13 and 14. FIG. 13 is a flowchart for explaining a procedure in the process performed by the X-ray CT apparatus 1 according to the first embodiment. FIG. 14 is a flowchart for explaining a procedure in the process performed by the X-ray CT apparatus 1 according to the modification example.

Steps S101, S102, and S107 to S109 in FIG. 13 are steps realized as a result of the processing circuitry 44 reading and executing the program corresponding to the controlling function 441 from the memory 41. Steps S103 and S104 in FIG. 13 are steps realized as a result of the processing circuitry 44 reading and executing the program corresponding to the estimating function 445 from the memory 41. Step S105 in FIG. 13 is a step realized as a result of the processing circuitry 44 reading and executing the program corresponding to the judging function 446 from the memory 41. Step S106 in FIG. 13 is a step realized as a result of the processing circuitry 44 reading and executing the program corresponding to the calculating function 447 from the memory 41.

As illustrated in FIG. 13, in the X-ray CT apparatus 1, the processing circuitry 44 at first performs a position determining scan (step S101) and calculates an initial temperature (step S102). Further, the processing circuitry 44 estimates a heat generation amount on the basis of the subject information and the scan condition (step S103) and estimates a temperature change to be observed when a main scan is performed on the basis of the initial temperature and the heat generation amount (step S104).

After that, the processing circuitry 44 judges whether or not it is possible to perform the main scan, on the basis of the estimated temperature change (step S105). When it is impossible to perform the main scan (step S105: No), the processing circuitry 44 calculates a waiting period until it becomes possible to perform the main scan (step S106) and causes the display 42 to display the calculated waiting period (step S107). On the contrary, when it is possible to perform the main scan (step S105: Yes), the processing circuitry 44 starts the main scan (step S109).

After causing the display 42 to display the waiting period at step S107, the processing circuitry 44 judges whether or not the waiting period has elapsed (step S108). When the waiting period has elapsed (step S108: Yes), the processing circuitry 44 starts the main scan (step S109). Conversely, unless the waiting period has elapsed, the processing circuitry 44 is in a standby state (step S108: No).

Steps S201, S202, and S207 to S209 in FIG. 14 are steps realized as a result of the processing circuitry 44 reading and executing the program corresponding to the controlling function 441 from the memory 41. Steps S203, S204, and S210 in FIG. 14 are steps realized as a result of the processing circuitry 44 reading and executing the program corresponding to the estimating function 445 from the memory 41. Step S205 in FIG. 14 is a step realized as a result of the processing circuitry 44 reading and executing the program corresponding to the judging function 446 from the memory 41. Step S206 in FIG. 14 is a step realized as a result of the processing circuitry 44 reading and executing the program corresponding to the calculating function 447 from the memory 41.

As illustrated in FIG. 14, in the X-ray CT apparatus 1, the processing circuitry 44 at first performs a position determining scan (step S201) and calculates an initial temperature while taking the ambient temperature into consideration (step S202). Further, on the basis of the subject information and the scan condition, the processing circuitry 44 estimates a heat generation amount (step S203) and estimates a temperature change to be observed when the main scan is performed on the basis of the initial temperature, the heat generation amount, and the ambient temperature (step S204).

After that, on the basis of the estimated temperature change, the processing circuitry 44 judges whether or not it is possible to perform the main scan (step S205). When it is impossible to perform the main scan (step S205: No), the processing circuitry 44 calculates a waiting period until it becomes possible to perform the main scan while taking the ambient temperature into consideration (step S206) and causes the display 42 to display the calculated waiting period (step S207). On the contrary, when it is possible to perform the main scan (step S205: Yes), the processing circuitry 44 starts the main scan (step S209).

After causing the display 42 to display the waiting period at step S207, the processing circuitry 44 judges whether or not the waiting period has elapsed (step S208). When the waiting period has elapsed (step S208: Yes), the processing circuitry 44 starts the main scan (step S209).

On the contrary, when the waiting period has not elapsed (step S208: No), the processing circuitry 44 judges whether or not the ambient temperature has changed (step S210). When the ambient temperature has changed (step S210: Yes), the processing circuitry 44 returns to step S204 and re-estimates a temperature change by using the post-change ambient temperature. After that, when it is impossible to perform the main scan at step S205, the processing circuitry 44 re-calculates a waiting period on the basis of the re-estimated temperature change and causes the display 42 to display the re-calculated waiting period. On the contrary, when the ambient temperature has not changed, the processing circuitry 44 continues to have the waiting period displayed (step S210: No).

As explained above, according to the first embodiment, the controlling function 441 is configured to obtain the initial temperature information of the X-ray detector 12 before the main scan, the information about the shape of the subject, and the scan condition of the main scan. The estimating function 445 is configured to estimate the temperature change of the X-ray detector 12 to be observed when the main scan is performed, on the basis of the initial temperature information, the information about the shape of the subject, and the information about the scan condition of the main scan. The judging function 446 is configured to judge whether or not it is possible to perform the main scan at the time of obtaining the initial temperature information, on the basis of the temperature change. Consequently, the X-ray CT apparatus 1 according to the first embodiment is able to perform the scan while taking the temperature increase of the X-ray detector 12 into consideration and thus makes it possible to efficiently proceed with the scan using the photon counting detector. Further, the X-ray CT apparatus 1 is able to exercise control so that the temperature of the X-ray detector 12 does not exceed the upper limit temperature and thus makes it possible to lower the possibility of the X-ray detector 12 experiencing malfunctions or performance changes due to the temperature increase.

Further, according to the first embodiment, the estimating function 445 is configured to estimate the heat generation amount of the X-ray detector 12 to be observed when the main scan is performed, on the basis of the information about the shape of the subject and the information about the scan condition of the main scan and to further estimate the temperature change on the basis of the initial temperature information and the heat generation amount. Consequently, the X-ray CT apparatus 1 according to the first embodiment makes it possible to judge whether or not it is possible to perform the main scan with an excellent level of precision.

Further, according to the first embodiment, the estimating function 445 is configured to estimate the heat generation amount of the X-ray detector to be observed when the main scan is performed further on the basis of the information about the ambient temperature of the X-ray detector 12 and to estimate the temperature change on the basis of the initial temperature information and the heat generation amount. Consequently, the X-ray CT apparatus 1 according to the first embodiment makes it possible to estimate the temperature change more accurately.

Further, according to the first embodiment, the estimating function 445 is configured to estimate the temperature of the X-ray detector 12 to be observed when the main scan is performed, on the basis of the initial temperature information and the temperature increase value based on the heat generation amount. Consequently, the X-ray CT apparatus 1 according to the first embodiment makes it possible to estimate the temperature of the X-ray detector 12 to be observed when the main scan is performed, with an excellent level of precision.

Further, according to the first embodiment, the judging function 446 is configured to compare the post-change temperature of the X-ray detector 12 with the threshold value and to determine that the main scan is to be performed when the post-change temperature will not exceed the threshold value. Consequently, the X-ray CT apparatus 1 according to the first embodiment makes it possible to exercise control so as not to exceed the upper limit temperature of the X-ray detector 12.

Further, according to the first embodiment, when the judgment result of the judging function 446 indicates that it is impossible to perform the main scan at the time of obtaining the initial temperature information, the calculating function 447 is configured to calculate the waiting period until the X-ray detector 12 reaches the temperature at which it is possible to perform the main scan. Consequently, the X-ray CT apparatus 1 according to the first embodiment is able to help understand the waiting period until it becomes possible to perform the main scan and thus makes it possible to efficiently proceed with the scan.

Further, according to the first embodiment, the calculating function 447 is configured to calculate the waiting period, further on the basis of the information about the ambient temperature of the X-ray detector 12. Consequently, the X-ray CT apparatus 1 according to the first embodiment makes it possible to calculate the waiting period more accurately.

Further, according to the first embodiment, the display 42 is configured to display the information about the waiting period. Consequently, the X-ray CT apparatus 1 according to the first embodiment makes it possible to help the operator understand the waiting period.

Further, according to the first embodiment, the controlling function 441 is configured to obtain the initial temperature information on the basis of the count rates of the X-ray detector 12 during the position determining scan or the temperature sensors. Consequently, the X-ray CT apparatus 1 according to the first embodiment makes it possible to obtain the initial temperature information easily.

Second Embodiment

In the first embodiment above, the example was explained in which the temperature change of the X-ray detector 12 is estimated so that, when it is impossible to perform the main scan, the waiting period is displayed. In a second embodiment, an example will be explained in which the scan condition is re-set when it is impossible to perform the main scan. In this situation, the X-ray CT apparatus 1 according to the second embodiment is different from that of the first embodiment for a process performed by the controlling function 441. The following sections will primarily explain the differences.

The controlling function 441 according to the second embodiment is configured to re-set the scan condition of the main scan, when the judgment result of the judging function 446 indicates that it is impossible to perform the main scan at the time of obtaining the initial temperature information. For example, together with the waiting period, the controlling function 441 causes the display 42 to display a GUI used for inputting whether or not the waiting period is to be accepted. In this situation, when the operator performs an operation to indicate that the waiting period is not to be accepted, the controlling function 441 is configured to re-set the scan condition and to exercise control so that the operator is presented with the re-set scan condition.

In this situation, the memory 41 has stored therein, in advance, a required minimum scan condition that guarantees image quality for each of various imaged sites. The controlling function 441 is configured to read a scan condition corresponding to the imaged site from the memory 41 and to cause the display 42 to display the read scan condition. When the controlling function 441 has re-set the scan condition, the calculating function 447 is configured to calculate a waiting period. The controlling function 441 is configured to exercise control again so that the display 42 displays the re-calculated waiting period.

Figure 15:
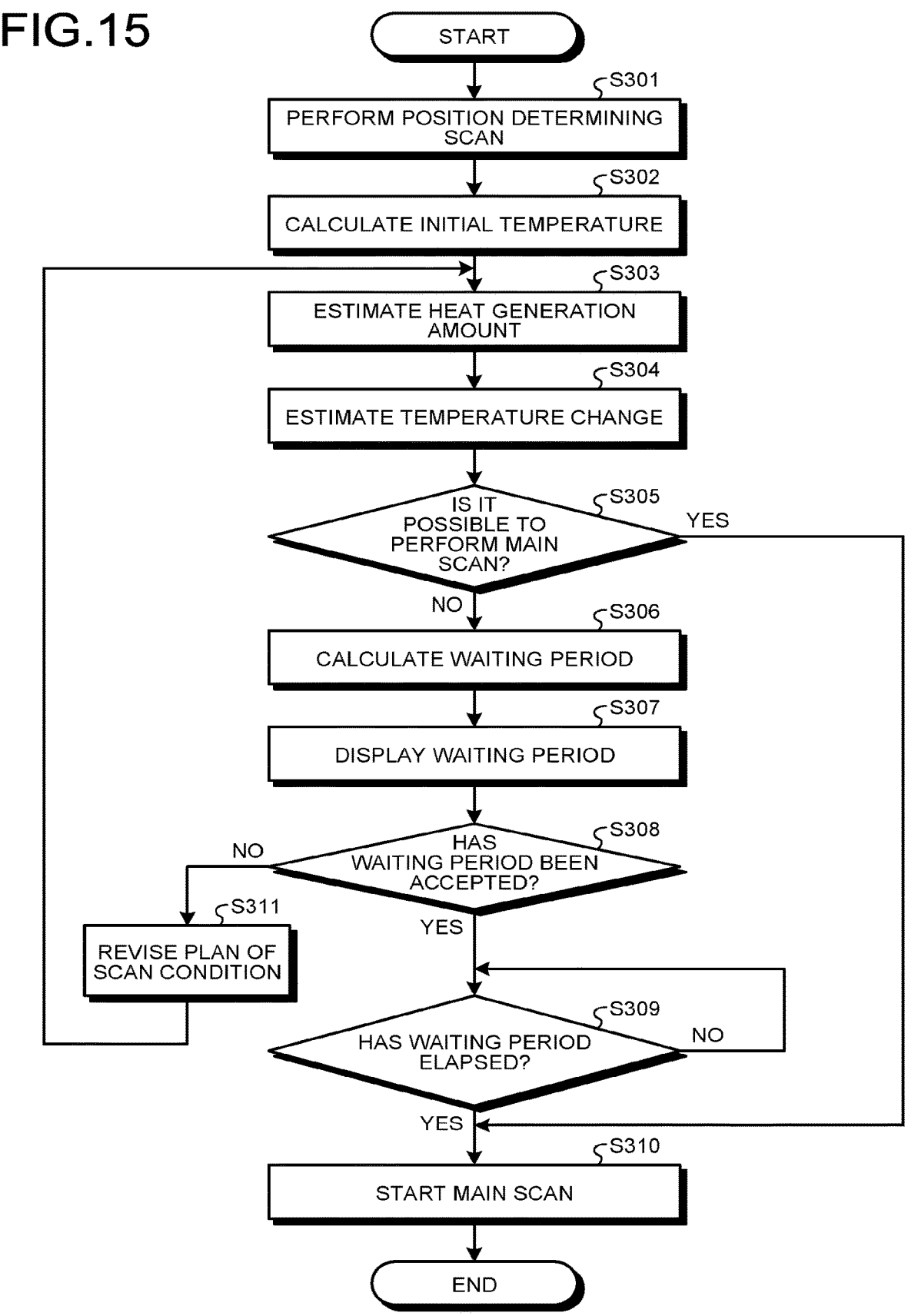
FIG. 15 is a flowchart for explaining a procedure in a process performed by an X-ray CT apparatus according to a second embodiment.

Next, a process performed by the X-ray CT apparatus 1 according to the second embodiment will be explained, with reference to FIG. 15. FIG. 15 is a flowchart for explaining a procedure in the process performed by the X-ray CT apparatus 1 according to the second embodiment.

Steps S301, S302, and S307 to S310 in FIG. 15 are steps realized as a result of the processing circuitry 44 reading and executing the program corresponding to the controlling function 441 from the memory 41. Steps S303 and S304 in FIG. 15 are steps realized as a result of the processing circuitry 44 reading and executing the program corresponding to the estimating function 445 from the memory 41. Step S305 in FIG. 15 is a step realized as a result of the processing circuitry 44 reading and executing the program corresponding to the judging function 446 from the memory 41. Step S306 in FIG. 15 is a step realized as a result of the processing circuitry 44 reading and executing the program corresponding to the calculating function 447 from the memory 41.

As illustrated in FIG. 15, in the X-ray CT apparatus 1, the processing circuitry 44 at first performs a position determining scan (step S301) and calculates an initial temperature (step S302). Further, the processing circuitry 44 estimates a heat generation amount on the basis of the subject information and the scan condition (step S303) and estimates a temperature change to be observed when the main scan is performed, on the basis of the initial temperature and the heat generation amount (step S304).

After that, the processing circuitry 44 judges whether or not it is possible to perform the main scan on the basis of the estimated temperature change (step S305). When it is impossible to perform the main scan (step S305: No), the processing circuitry 44 calculates a waiting period until it becomes possible to perform the main scan (step S306) and causes the display 42 to display the calculated waiting period (step S307). On the contrary, when it is possible to perform the main scan (step S305: Yes), the processing circuitry 44 starts the main scan (step S310).

After causing the display 42 to display the waiting period at step S307, the processing circuitry 44 judges whether or not the waiting period is accepted (step S308). When the waiting period is not accepted (step S308: No), the processing circuitry 44 revises the plan of the scan condition (step S311) and returns to step S303 to estimate a heat generation amount. On the contrary, when the waiting period is accepted (step S308: Yes), the processing circuitry 44 judges whether or not the waiting period has elapsed (step S309). When the waiting period has elapsed (step S309: Yes), the processing circuitry 44 starts the main scan (step S310). Conversely, unless the waiting period has elapsed, the processing circuitry 44 is in a standby state (step S309: No).

Although FIG. 15 illustrates the process in which the ambient temperature is not taken into consideration, possible embodiments are not limited to this example. It is also acceptable to calculate a temperature change and a waiting period while taking the ambient temperature into consideration. In other words, the processing circuitry 44 according to the second embodiment is also capable of performing the processing steps illustrated in FIG. 14 in combination, as appropriate.

As explained above, according to the second embodiment, the controlling function 441 is configured to re-set the scan condition of the main scan, when the judgment result of the judging function 446 indicates that it is impossible to perform the main scan at the time of obtaining the initial temperature information. Consequently, the X-ray CT apparatus 1 according to the second embodiment makes it possible to shorten the waiting period by revising the plan of the scan condition.

Third Embodiment

In the first embodiment above, the example was explained in which the temperature change of the X-ray detector 12 is estimated so as to display the waiting period when it is impossible to perform the main scan. In a third embodiment, an example will be explained in which, in addition to the waiting period for the X-ray detector 12, a waiting period for the X-ray tube 11 is taken into account. In this situation, the X-ray CT apparatus 1 according to the third embodiment is different from that of the first embodiment for processes performed by the controlling function 441 and the judging function 446. The following sections will primarily explain the differences.

In the X-ray tube 11, heat is accumulated in the target with which the thermo electrons generated at the negative pole collide. The heat accumulated in the target may cause changes in the performance. For this reason, the X-ray CT apparatus 1 has a protecting function that provides a waiting period to let the heat of the target fall, for the purpose of protecting the X-ray tube 11. Thus, while taking into consideration both the waiting period related to the X-ray detector 12 and the waiting period related to the X-ray tube 11, the X-ray CT apparatus 1 according to the third embodiment is configured to judge whether or not it is possible to perform the main scan and to display a waiting period.

The controlling function 441 according to the third embodiment is configured to further obtain information about a waiting period until the X-ray tube reaches a temperature at which it is possible to perform the main scan. For example, the controlling function 441 is configured to calculate the waiting period on the basis of the voltage applied from the X-ray high-voltage device 14 and the time period during which the thermo electrons are emitted toward the target.

On the basis of the temperature change of the X-ray detector 12 and the waiting period until the X-ray tube 11 reaches the temperature at which it is possible to perform the main scan, the judging function 446 according to the third embodiment is configured to judge whether or not it is possible to perform the main scan at the time of obtaining the initial temperature information. More specifically, the judging function 446 is configured to judge whether or not the post-change temperature of the X-ray detector 12 exceeds a threshold value and to also judge whether or not there is a waiting period related to the X-ray tube 11.

In this situation, when the post-change temperature of the X-ray detector 12 does not exceed the threshold value, while there is no waiting period related to the X-ray tube 11, the judging function 446 determines that it is possible to perform the main scan. In other words, the judging function 446 determines that it is impossible to perform the main scan when one or both of the following are true: the post-change temperature of the X-ray detector 12 exceeds the threshold value; and there is a waiting period related to the X-ray tube 11.

Further, the controlling function 441 causes the display 42 to display information about the longer of the two waiting periods, namely, the waiting period until the X-ray detector 12 reaches the temperature at which it is possible to perform the main scan and the waiting period until the X-ray tube 11 reaches the temperature at which it is possible to perform the main scan. For example, when the post-change temperature of the X-ray detector 12 exceeds the threshold value, while there is no waiting period related to the X-ray tube 11, the controlling function 441 causes the display 42 to display the waiting period calculated by the calculating function 447. In another example, when the post-change temperature of the X-ray detector 12 does not exceed the threshold value, while there is a waiting period related to the X-ray tube 11, the controlling function 441 causes the display 42 to display the waiting period related to the X-ray tube 11. In yet another example, when the post-change temperature of the X-ray detector 12 exceeds the threshold value, while there is a waiting period related to the X-ray tube 11, the controlling function 441 causes the display 42 to display the longer of the two waiting periods, namely, the waiting period calculated by the calculating function 447 and the waiting period related to the X-ray tube 11.

In this situation, the controlling function 441 according to the third embodiment is capable of revising the plan of the scan condition as explained in the second embodiment. For example, when there is a waiting period related to the X-ray tube 11, the controlling function 441 revises the plan of the scan condition while taking the waiting period for the X-ray tube 11 into consideration.

Figure 16:
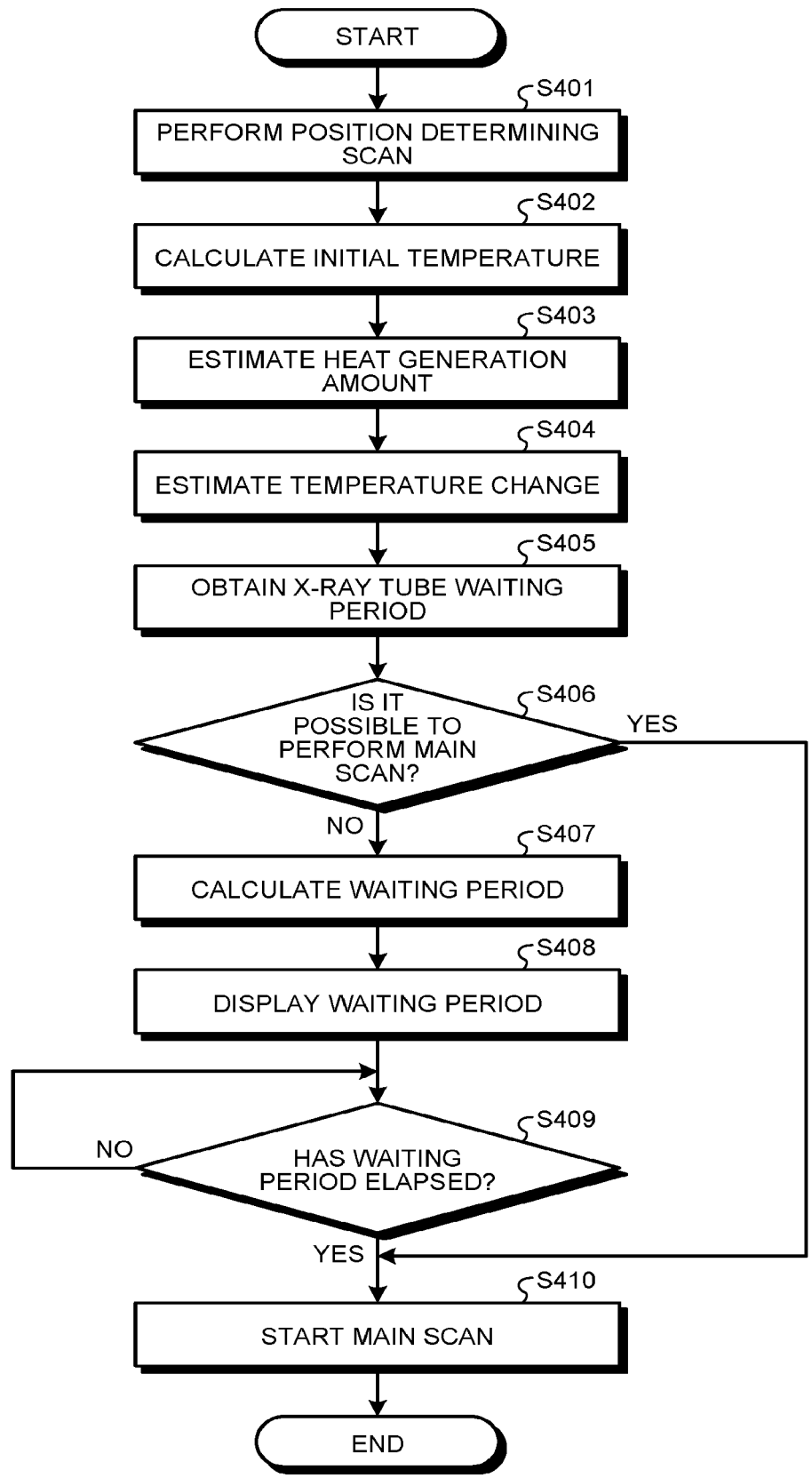
FIG. 16 is a flowchart for explaining a procedure in a process performed by an X-ray CT apparatus according to a third embodiment.

Next, a process performed by the X-ray CT apparatus 1 according to the third embodiment will be explained, with reference to FIG. 16. FIG. 16 is a flowchart for explaining a procedure in the process performed by the X-ray CT apparatus 1 according to the third embodiment.

Steps S401, S402, S405, S408 to S410 in FIG. 16 are steps realized as a result of the processing circuitry 44 reading and executing the program corresponding to the controlling function 441 from the memory 41. Steps S403 and S404 in FIG. 16 are steps realized as a result of the processing circuitry 44 reading and executing the program corresponding to the estimating function 445 from the memory 41. Step S406 in FIG. 16 is a step realized as a result of the processing circuitry 44 reading and executing the program corresponding to the judging function 446 from the memory 41. Step S407 in FIG. 16 is a step realized as a result of the processing circuitry 44 reading and executing the program corresponding to the calculating function 447 from the memory 41.

As illustrated in FIG. 16, in the X-ray CT apparatus 1, the processing circuitry 44 at first performs a position determining scan (step S401) and calculates an initial temperature (step S402). Further, the processing circuitry 44 estimates a heat generation amount on the basis of the subject information and the scan condition (step S403) and estimates a temperature change to be observed when the main scan is performed, on the basis of the initial temperature and the heat generation amount (step S404). Further, the processing circuitry 44 obtains information about the waiting period for the X-ray tube 11 (step S405).

After that, on the basis of the estimated temperature change and the obtained information about the waiting period, the processing circuitry 44 judges whether or not it is possible to perform the main scan (step S406). When it is impossible to perform the main scan (step S406: No), the processing circuitry 44 calculates the waiting period until it becomes possible to perform the main scan (step S407) and causes the display 42 to display the calculated waiting period (step S408). When there are waiting periods for both the X-ray tube 11 and the X-ray detector 12, the processing circuitry 44 causes the display 42 to display the longer of the two waiting periods. On the contrary, when it is possible to perform the main scan (step S406: Yes), the processing circuitry 44 starts the main scan (step S410).

After causing the display 42 to display the waiting period at step S408, the processing circuitry 44 judges whether or not the waiting period has elapsed (step S409). When the waiting period has elapsed (step S409: Yes), the processing circuitry 44 starts the main scan (step S410). Conversely, unless the waiting period has elapsed, the processing circuitry 44 is in a standby state (step S409: No).

Although FIG. 16 illustrates the process performed when the ambient temperature is not taken into consideration, and the plan of the scan condition is not revised, possible embodiments are not limited to this example. It is also acceptable to calculate a temperature change and a waiting period while taking the ambient temperature into consideration and to also revise the plan of the scan condition. In other words, the processing circuitry 44 according to the third embodiment is also capable of performing the processing steps illustrated in FIGS. 14 and 15 in combination, as appropriate.

As explained above, according to the third embodiment, the controlling function 441 is configured to further obtain the information about the waiting period until the X-ray tube 11 reaches the temperature at which it is possible to perform the main scan. The display 42 is configured to display the information about the longer of the two waiting periods, namely, the waiting period until the X-ray detector 12 reaches the temperature at which it is possible to perform the main scan and the waiting period until the X-ray tube 11 reaches the temperature at which it is possible to perform the main scan. Consequently, the X-ray CT apparatus 1 according to the third embodiment is able to help the operator understand the waiting period that takes the waiting period related to the X-ray tube 11 into consideration, in addition to the waiting period related to the X-ray detector 12 and to thus make it possible to efficiently proceed with the scan.

Further, according to the third embodiment, the controlling function 441 is configured to further obtain the information about the waiting period until the X-ray tube 11 reaches the temperature at which it is possible to perform the main scan. The judging function 446 is configured to judge whether or not it is possible to perform the main scan at the time of obtaining the initial temperature information, on the basis of the temperature change of the X-ray detector 12 and the waiting period until the X-ray tube 11 reaches the temperature at which it is possible to perform the main scan. Consequently, the X-ray CT apparatus 1 according to the third embodiment is able to take the waiting period related to the X-ray tube 11 into consideration, in addition to the waiting period related to the X-ray detector 12 and thus makes it possible to more efficiently proceed with the scan.

Fourth Embodiment

In the embodiments described above, the example was explained in which the temperature change of the X-ray detector 12 is estimated before the main scan is performed, so as to display the waiting period when it is impossible to perform the main scan. In a fourth embodiment, an example will be explained in which a temperature change is estimated also while the main scan is being executed. The X-ray CT apparatus 1 according to the fourth embodiment is different from that of the first embodiment for processes performed by the controlling function 441 and the judging function 446. The following sections will primarily explain the differences.

The controlling function 441 according to the fourth embodiment is configured to further obtain temperature information of the X-ray detector 12 from during the main scan. For example, the controlling function 441 is configured to chronologically obtain count rates during the main scan, in a real-time manner. When the controlling function 441 has obtained the count rates from during the main scan, the estimating function 445 estimates temperature changes of the X-ray detector 12. In other words, the estimating function 445 is configured to estimate the real-time temperature changes of the X-ray detector 12 during the main scan.

When the estimating function 445 has estimated the temperature changes during the main scan, the judging function 446 is configured to judge whether or not the temperature of the X-ray detector 12 will exceed a threshold value. For example, the judging function 446 judges whether or not the temperature changes during the main scan estimated by the estimating function 445 exhibit a larger temperature increase than the temperature change estimated before the main scan and make the temperature of the X-ray detector 12 exceed the threshold value before the end of the main scan.

In this situation, when the temperature of the X-ray detector 12 would exceed the threshold value, the judging function 446 is configured to judge whether or not the main scan is to be continued, on the basis of the time period until the end of the main scan. More specifically, when determining that the temperature of the X-ray detector 12 would exceed the threshold value, the judging function 446 is configured to calculate the time period from the judging point in time to the end of the main scan and to further judge whether or not the calculated time period is within a tolerance range (exceeds a threshold value).

In this situation, when the time period until the end of the main scan does not exceed the threshold value, the judging function 446 determines that the main scan is to be continued. In other words, when determining that the excess of the temperature of the X-ray detector 12 beyond the upper limit temperature is relatively small, the judging function 446 determines that the main scan is to be continued.

On the contrary, when the time period until the end of the main scan exceeds the threshold value, the judging function 446 determines to execute one of the following: changing the scan condition; stopping a part of the operations of the X-ray detector 12; and cancelling the main scan. In other words, when determining that the excess of the temperature of the X-ray detector 12 beyond the upper limit temperature is relatively large, the judging function 446 is configured to determine to execute the one of the following: changing the scan condition; stopping a part of the operations of the X-ray detector 12; and cancelling the main scan.

For example, on the basis of one or both of a temperature increase tendency of the X-ray detector 12 and medical examination details of the main scan, the judging function 446 determines to execute the one of the following: changing the scan condition; stopping a part of the operations of the X-ray detector 12; and cancelling the main scan.

In one example, the judging function 446 determines to cancel the main scan when a temperature increase rate (a temperature increase per unit time period) exceeds a threshold value or when the medical examination allows a re-scan. In other words, the judging function 446 determines to cancel the main scan, when the excess of the temperature of the X-ray detector 12 beyond the upper limit temperature is determined to become larger or when the burden to be imposed on the subject by the re-scan will not be great.

In contrast, for example, the judging function 446 determines to change the scan condition or to stop a part of the operations of the X-ray detector 12, when the temperature increase rate does not exceed the threshold value or when the medical examination has such a nature that it would be difficult to perform a re-scan. For example, when details of the medical examination indicate a contrast-enhanced imaging examination or the like, the judging function 446 determines to change the scan condition or to stop a part of the operations of the X-ray detector 12.

In one example, to change the scan condition, the judging function 446 determines to suppress the radiation dose or to shorten the scan time period. Alternatively, the judging function 446 may determine to stop operations of only one or more of the ASICs 122. In this situation, for example, the judging function 446 stops operations of such ASICs 122 that correspond to the detecting elements positioned in the interface part between the subject and the air.

In the embodiment above, the example was explained in which the count rates are obtained as the information about the temperature of the X-ray detector 12 during the main scan; however, possible embodiments are not limited to this example. For instance, temperature information acquired by a temperature sensor may be obtained. In that situation, the X-ray detector 12 is provided with the temperature sensors 123 so that the controlling function 441 obtains temperature information detected by the temperature sensors 123 during the main scan.

Figure 17:
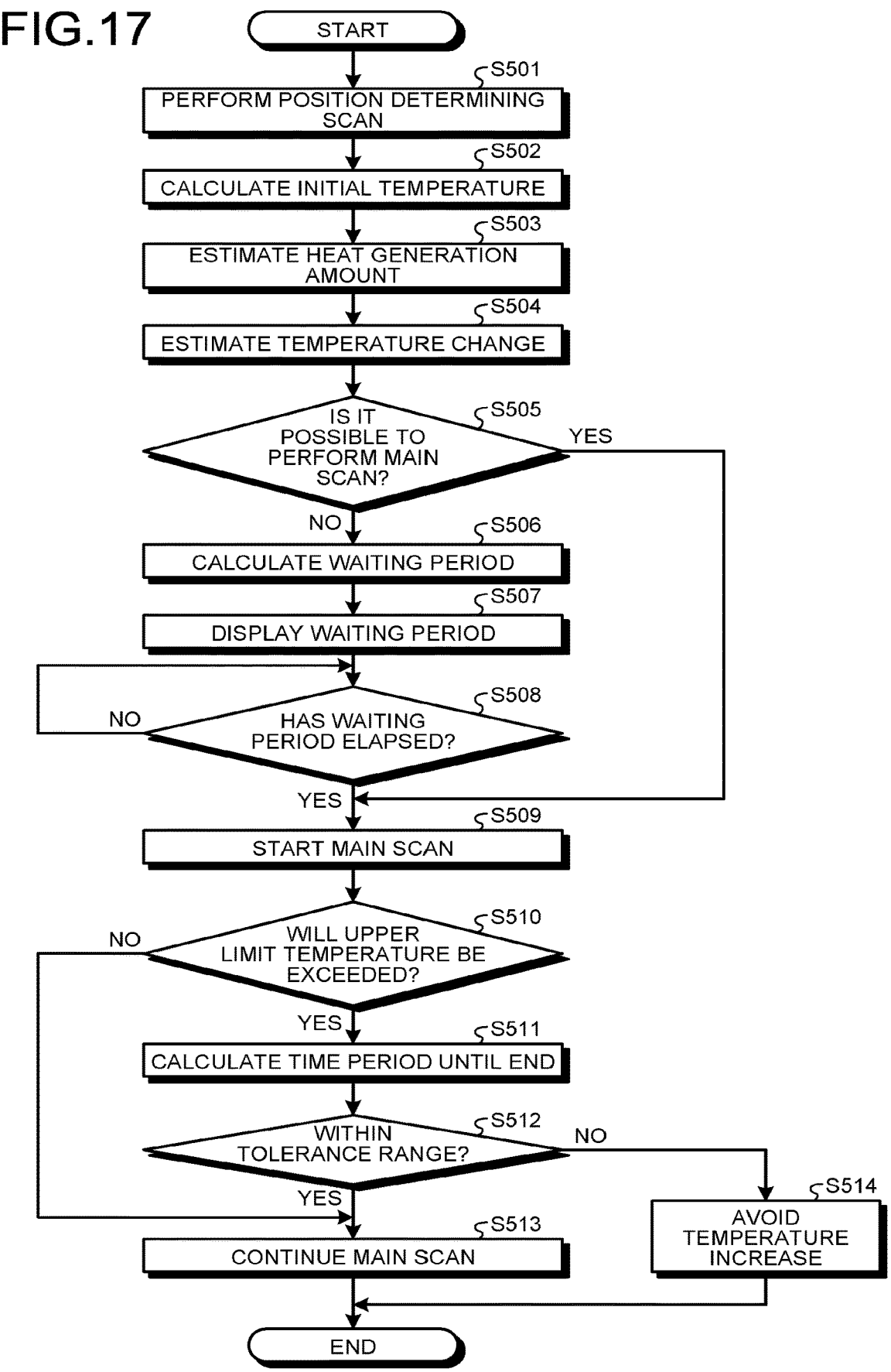
FIG. 17 is a flowchart for explaining a procedure in a process performed by an X-ray CT apparatus according to a fourth embodiment.

Next, a process performed by the X-ray CT apparatus 1 according to the fourth embodiment will be explained, with reference to FIG. 17. FIG. 17 is a flowchart for explaining a procedure in the process performed by the X-ray CT apparatus 1 according to the fourth embodiment.

Steps S501, S502, and S507 to S509 in FIG. 17 are steps realized as a result of the processing circuitry 44 reading and executing the program corresponding to the controlling function 441 from the memory 41. Steps S503 and S504 in FIG. 17 are steps realized as a result of the processing circuitry 44 reading and executing the program corresponding to the estimating function 445 from the memory 41. Steps S505 and S510 to S514 in FIG. 17 are steps realized as a result of the processing circuitry 44 reading and executing the program corresponding to the judging function 446 from the memory 41. Step S506 in FIG. 17 is a step realized as a result of the processing circuitry 44 reading and executing the program corresponding to the calculating function 447 from the memory 41.

As illustrated in FIG. 17, in the X-ray CT apparatus 1, the processing circuitry 44 at first performs a position determining scan (step S501) and calculates an initial temperature (step S502). Further, on the basis of the subject information and the scan condition, the processing circuitry 44 estimates a heat generation amount (step S503) and estimates a temperature change to be observed when the main scan is performed on the basis of the initial temperature and the heat generation amount (step S504).

After that, on the basis of the estimated temperature change and the obtained information about the waiting period, the processing circuitry 44 judges whether or not it is possible to perform the main scan (step S505). When it is impossible to perform the main scan (step S505: No), the processing circuitry 44 calculates a waiting period until it becomes possible to perform the main scan (step S506) and causes the display 42 to display the calculated waiting period (step S507). On the contrary, when it is possible to perform the main scan (step S505: Yes), the processing circuitry 44 starts the main scan (step S509).

After causing the display 42 to display the waiting period at step S507, the processing circuitry 44 judges whether or not the waiting period has elapsed (step S508). When the waiting period has elapsed (step S508: Yes), the processing circuitry 44 starts the main scan (step S509). Conversely, unless the waiting period has elapsed, the processing circuitry 44 is in a standby state (step S508: No).

Further, when the main scan is started at step S509, the processing circuitry 44 obtains the information about the temperature of the X-ray detector 12 and judges whether or not the upper limit temperature will be exceeded (step S510). When the upper limit temperature will not be exceeded (step S510: No), the processing circuitry 44 continues the main scan (step S513).

On the contrary, when the upper limit temperature would be exceeded (step S510: Yes), the processing circuitry 44 calculates the time period until the end of the main scan (step S511) and judges whether or not the calculated time period is within a tolerance range (step S512). When the time period is within the tolerance range (does not exceed a threshold value) (step S512: Yes), the processing circuitry 44 continues the scan (step S513).

On the contrary, when the time period is within the tolerance range (exceeds a threshold value) (step S512: No), the processing circuitry 44 avoids the temperature increase of the X-ray detector 12 by executing one of the following: changing the scan condition; stopping operations of one or more of the ASICs 122; and cancelling the main scan (step S514).

In this situation, the processing circuitry 44 according to the fourth embodiment is also capable of performing the processing steps illustrated in FIGS. 14 to 16 in combination, as appropriate.

As explained above, according to the fourth embodiment, the controlling function 441 is configured to further obtain the temperature information of the X-ray detector 12 during the scan. When the temperature of the X-ray detector 12 would exceed the threshold value, the judging function 446 is configured to judge whether or not the main scan is to be continued on the basis of the time until the end of the main scan. Consequently, the X-ray CT apparatus 1 according to the fourth embodiment makes it possible to respond in accordance with actual situations by monitoring the temperature of the X-ray detector 12 even during the main scan.

Further, according to the fourth embodiment, when the time period until the end of the main scan exceeds the threshold value, the judging function 446 determines to execute one of the following: changing the scan condition; stopping a part of the operations of the X-ray detector 12; and cancelling the main scan. Consequently, the X-ray CT apparatus 1 according to the fourth embodiment makes is possible to avoid an excessive temperature increase during the main scan.

Further, according to the fourth embodiment, on the basis of one or both of the temperature increase tendency of the X-ray detector 12 and the medical examination details of the main scan, the judging function 446 determines to execute one of the following: changing the scan condition; stopping a part of the operations of the X-ray detector; and cancelling the main scan. Consequently, the X-ray CT apparatus 1 according to the fourth embodiment is able to address situations while taking into consideration the actual temperature increase tendency during the main scan and the burden imposed on the subject and thus makes is possible to perform appropriate processes in response to the temperature increase of the X-ray detector 12.

Fifth Embodiment

In the embodiments above, the processes based on the premise where the center of the subject matches the center of the field of view was explained. In a fifth embodiment, an example will be explained in which it is judged whether or not the center of the subject matches the center of the field of view. In the present example, the X-ray CT apparatus 1 according to the fifth embodiment is different from that of the first embodiment for processes performed by the controlling function 441 and the judging function 446. The following sections will primarily explain the differences.

The controlling function 441 according to the fifth embodiment is configured to further obtain position information of the subject. For example, the controlling function 441 is configured to obtain information about the position of the subject in the Field of View (FOV) on the basis of a position determining image taken by performing a position determining scan.

The judging function 446 according to the fifth embodiment is configured to judge whether or not there is a misalignment between the center position of the subject and the center of the field of view. More specifically, the judging function 446 is configured to judge whether or not the center position of the subject and the center of the field of view match and, when the two do not match, to calculate a misalignment amount.

Figure 18:
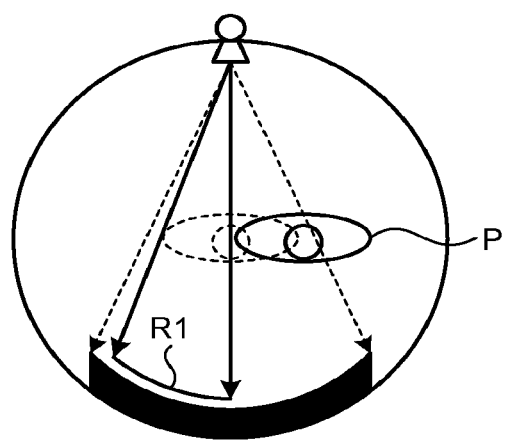
FIG. 18 is a drawing for explaining a process performed by a judging function according to a fifth embodiment.

FIG. 18 is a drawing for explaining a process performed by the judging function 446 according to the fifth embodiment. For example, the judging function 446 judges whether or not the position of the subject P is misaligned with the center of the field of view. When the position of the subject P is misaligned with the center of the field of view as illustrated in FIG. 18, the X-rays that are supposed to be radiated by the subject P become incident to the X-ray detector 12 without passing through the subject P. In other words, X-rays in an amount larger than expected become incident to a region R1 in FIG. 18. In that situation, because the temperature change cannot be estimated correctly, it may not be possible, in some situations, to correctly judge whether or not the temperature will exceed the upper limit temperature.

To cope with this situation, when the center position of the subject does not match the center of the field of view, and a misalignment amount has been calculated, the controlling function 441 causes the display 42 to display information about the misalignment of positions. For example, the controlling function 441 causes the display 42 to display warning information indicating that the misalignment of positions has occurred and/or the direction of the misalignment and the misalignment amount.

Further, the controlling function 441 is configured to move the position of the subject, on the basis of the misalignment amount of the center position of the subject from the center of the field of view. For example, the controlling function 441 moves the position of the subject so that the center position of the subject matches the center of the field of view, by controlling the table 30 on the basis of the direction of the misalignment and the misalignment amount.

In this situation, the control exercised by the controlling function 441 to move the subject may automatically be implemented or may be implemented in accordance with operations performed by the operator. In this situation, when the moving control is exercised in accordance with the operations performed by the operator, the controlling function 441 may exercise control so that the display 42 displays information indicating a moving direction and a moving amount of the tabletop 33 and/or so that a projector outputs a projection line used for aligning the center position of the subject.

Figure 19:
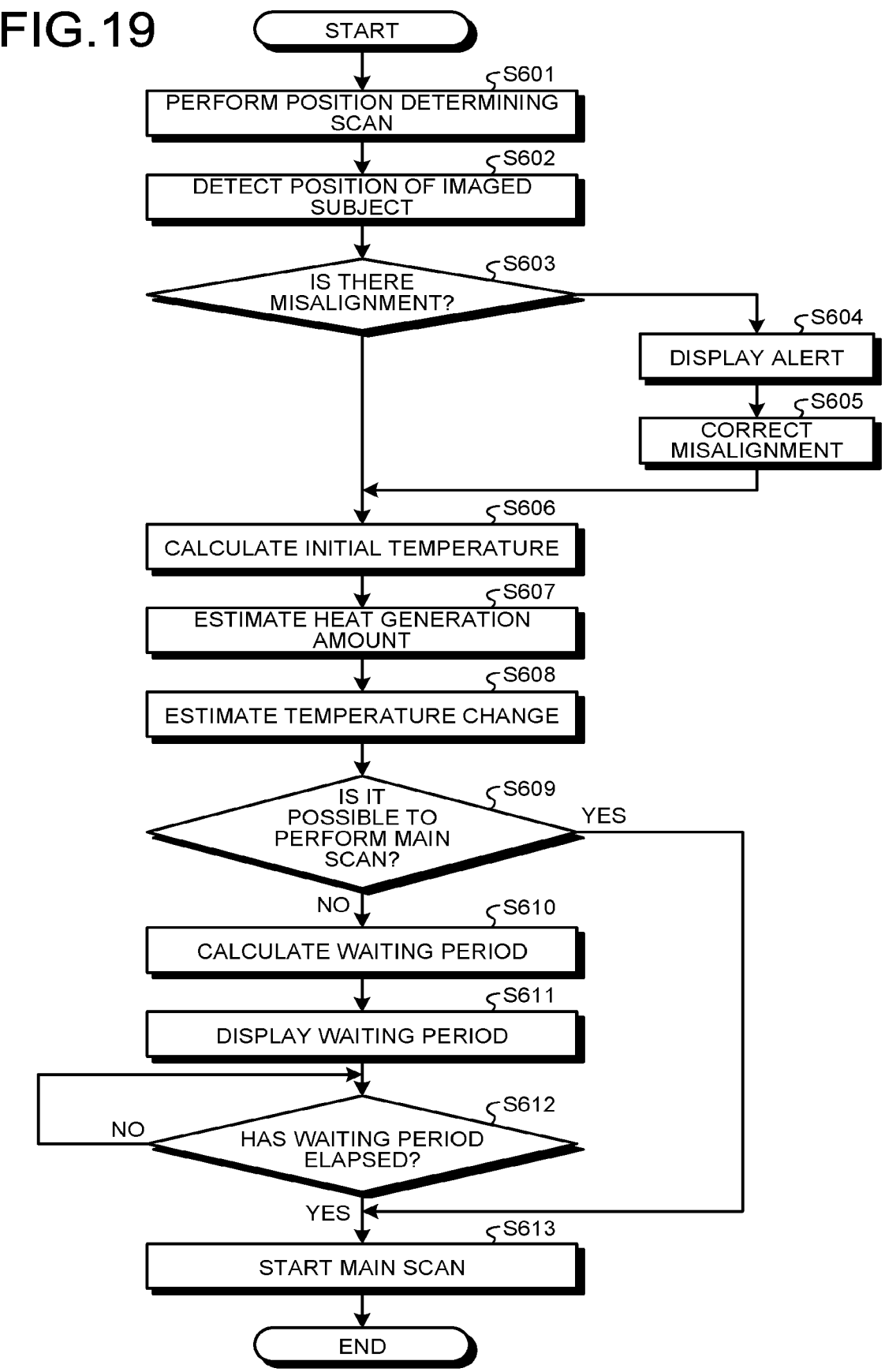
FIG. 19 is a flowchart for explaining a procedure in a process performed by an X-ray CT apparatus according to the fifth embodiment.

Next, a process performed by the X-ray CT apparatus 1 according to the fifth embodiment will be explained, with reference to FIG. 19. FIG. 19 is a flowchart for explaining a procedure in the process performed by the X-ray CT apparatus 1 according to the fifth embodiment.

Steps S601, S602, S604 to S606, and S611 to S613 in FIG. 19 are steps realized as a result of the processing circuitry 44 reading and executing the program corresponding to the controlling function 441 from the memory 41. Steps S607 and S608 in FIG. 19 are steps realized as a result of the processing circuitry 44 reading and executing the program corresponding to the estimating function 445 from the memory 41. Steps S603 and S609 in FIG. 19 are steps realized as a result of the processing circuitry 44 reading and executing the program corresponding to the judging function 446 from the memory 41. Step S610 in FIG. 19 is a step realized as a result of the processing circuitry 44 reading and executing the program corresponding to the calculating function 447 from the memory 41.

As illustrated in FIG. 19, in the X-ray CT apparatus 1, the processing circuitry 44 at first performs a position determining scan (step S601), detects the position of the subject (step S602), and judges whether or not there is a misalignment of positions (step S603). When there is a misalignment of positions (step S603: Yes), the processing circuitry 44 causes the display 42 to display an alert (step S604) and corrects the misalignment of positions (step S605).

On the contrary, when there is no misalignment of positions (step S603: No) or when the misalignment of positions has been corrected, the processing circuitry 44 calculates an initial temperature (step S606). Further, the processing circuitry 44 estimates a heat generation amount on the basis of the subject information and the scan condition (step S607) and estimates a temperature change to be observed when the main scan is performed, on the basis of the initial temperature and the heat generation amount (step S608).

After that, the processing circuitry 44 judges whether or not it is possible to perform the main scan, on the basis of the estimated temperature change (step S609). When it is impossible to perform the main scan (step S609: No), the processing circuitry 44 calculates a waiting period until it becomes possible to perform the main scan (step S610) and causes the display 42 to display the calculated waiting period (step S611). On the contrary, when it is possible to perform the main scan (step S609: Yes), the processing circuitry 44 starts the main scan (step S613).

After causing the display 42 to display the waiting period at step S611, the processing circuitry 44 judges whether or not the waiting period has elapsed (step S612). When the waiting period has elapsed (step S612: Yes), the processing circuitry 44 starts the main scan (step S613). Conversely, unless the waiting period has elapsed, the processing circuitry 44 is in a standby state (step S612: No).

In this situation, the processing circuitry 44 according to the fifth embodiment is also capable of performing the processing steps illustrated in FIGS. 14 to 17 in combination, as appropriate.

As explained above, according to the fifth embodiment, the controlling function 441 is configured to further obtain the position information of the subject. The judging function 446 is configured to judge whether or not there is a misalignment between the center position of the subject and the center of the field of view. When the center position of the subject is misaligned with the center of the field of view, the display 42 is configured to display the information about the misalignment of positions. Consequently, the X-ray CT apparatus 1 according to the fifth embodiment makes it possible to accurately estimate the temperature changes.

Further, according to the fifth embodiment, the controlling function 441 is configured to move the position of the subject on the basis of the misalignment amount of the center position of the subject from the center of the field of view. Consequently, the X-ray CT apparatus 1 according to the fifth embodiment makes it possible to correct the misalignment of positions.

Other Embodiments

The first to the fifth embodiments have thus been explained. It is also possible to carry out the present disclosure in various modes different from those in the first to the fifth embodiments described above.

In the fifth embodiment above, the example was explained in which the X-ray CT apparatus 1 is configured to perform both the process related to the misalignment of the position of the subject and the process related to the temperature change of the X-ray detector 12; however, possible embodiments are not limited to this example. The X-ray CT apparatus 1 may be configured to perform only the process related to the misalignment of the position of the subject.

Figure 20:
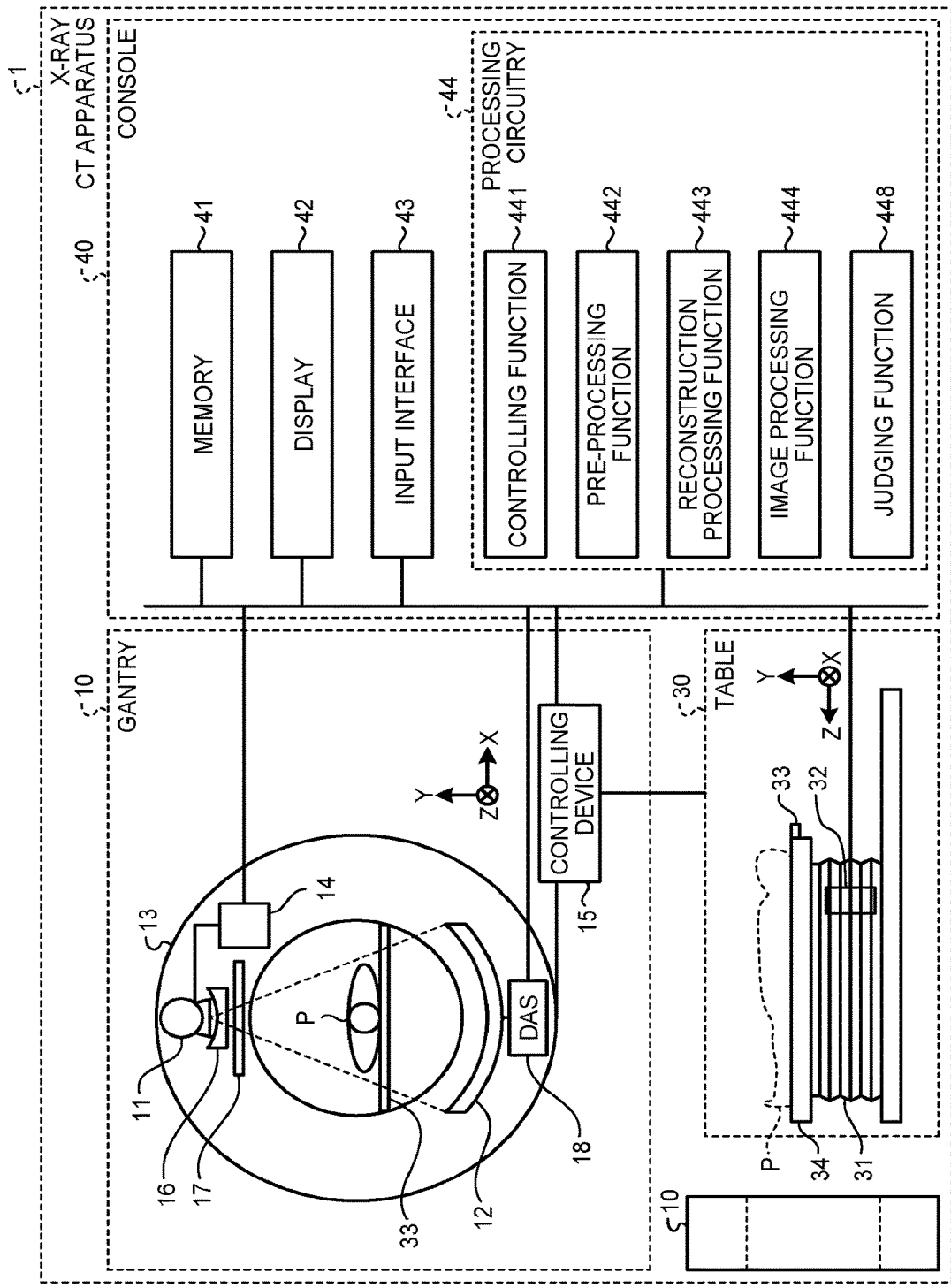
FIG. 20 is a diagram illustrating an exemplary configuration of an X-ray CT apparatus according to another embodiment.

FIG. 20 is a diagram illustrating an exemplary configuration of the X-ray CT apparatus 1 according to another embodiment. As illustrated in FIG. 20, the X-ray CT apparatus 1 according to the other embodiment is different from the X-ray CT apparatus 1 in FIG. 1 for not including the estimating function 445, the judging function 446, and the calculating function 447, but including a judging function 448. The following sections will primarily explain the differences. Some of the constituent elements that are the same will be referred to by using the same reference characters, and duplicate explanations thereof will be omitted.

The controlling function 441 according to the other embodiment is configured to obtain the position information of the subject with respect to the X-ray detector 12. For example, the controlling function 441 is configured to obtain information about the position of the subject in the FOV, on the basis of a position determining image taken by performing a position determining scan.

The judging function 448 according to the other embodiment is configured to judge whether or not there is a misalignment between the center position of the subject and the center of the field of view. More specifically, the judging function 448 is configured to judge whether or not the center position of the subject and the center of the field of view match and, when the two do not match, to calculate a misalignment amount.

When the center position of the subject does not match the center of the field of view, and the misalignment amount has been calculated, the controlling function 441 causes the display 42 to display information about the misalignment of positions. For example, the controlling function 441 causes the display 42 to display warning information indicating that the misalignment of positions has occurred and/or the direction of the misalignment and the misalignment amount.

Further, on the basis of the misalignment amount of the center position of the subject from the center of the field of view, the controlling function 441 is configured to move the position of the subject. For example, the controlling function 441 moves the position of the subject so that the center position of the subject matches the center of the field of view, by controlling the table 30 on the basis of the direction of the misalignment and the misalignment amount.

In this situation, the control exercised by the controlling function 441 to move the subject may automatically be implemented or may be implemented in accordance with operations performed by the operator. In this situation, when the moving control is exercised in accordance with the operations performed by the operator, the controlling function 441 may exercise control so that the display 42 displays information indicating a moving direction and a moving amount of the tabletop 33 and/or so that a projector outputs a projection line used for aligning the center position of the subject.

As explained above, the controlling function 441 is configured to obtain the position information of the subject. The judging function 448 is configured to judge whether or not there is a misalignment between the center position of the subject and the center of the field of view. When the center position of the subject is misaligned with the center of the field of view, the display 42 is configured to display the information about the misalignment of positions. Consequently, the X-ray CT apparatus 1 according to the other embodiment makes it possible to provide the information about the misalignment of positions.

Further, the controlling function 441 is configured to move the position of the subject, on the basis of the misalignment amount of the center position of the subject from the center of the field of view. Consequently, the X-ray CT apparatus 1 according to the other embodiment makes it possible to correct the misalignment of positions.

Further, in the embodiments above, the example was explained in which the processing circuitry 44 executes the plurality of functions; however, possible embodiments are not limited to this example. For instance, another arrangement is also acceptable in which two or more of the functions are provided in the console 40 as independent circuits, so that each of the circuits executes a corresponding one of the functions.

The constituent elements of the apparatuses and the devices in the drawings of the above embodiments are based on functional concepts. Thus, it is not necessary to physically configure the constituent elements as indicated in the drawings. In other words, specific modes of distribution and integration of the apparatuses and the devices are not limited to those illustrated in the drawings. It is acceptable to functionally or physically distribute or integrate all or a part of the apparatuses and the devices in any arbitrary units, depending on various loads and the status of use. Further, all or an arbitrary part of the processing functions performed by the apparatuses and the devices may be realized by a CPU and a program analyzed and executed by the CPU or may be realized as hardware using wired logic.

Further, with regard to the processes explained in the embodiments above, it is acceptable to manually perform a part of the processes described as being performed automatically. Conversely, by using a publicly-known method, it is also acceptable to automatically perform all or a part of the processes described as being performed manually. Further, unless noted otherwise, it is acceptable to arbitrarily modify any of the processing procedures, the controlling procedures, specific names, and various information including various types of data and parameters that are presented in the above text and the drawings.

The term "processor" used in the above explanations denotes, for example, a Central Processing Unit (CPU), a Graphics Processing Unit (GPU), or a circuit such as an Application Specific Integrated Circuit (ASIC) or a programmable logic device (e.g., a Simple Programmable Logic Device [SPLD], a Complex Programmable Logic Device [CPLD], or a Field Programmable Gate Array [FPGA]). The one or more processors realize the functions by reading and executing the programs saved in the memory 41. Further, instead of saving the programs in the memory 41, it is also acceptable to directly incorporate the programs into the circuits of the processors. In that situation, the processors realize the functions by reading and executing the programs incorporated in the circuits thereof. Further, each of the processors in the present embodiments does not necessarily have to be structured as a single circuit. It is also acceptable to structure one processor by combining together a plurality of independent circuits so as to realize the functions thereof. Further, it is also acceptable to integrate two or more of the constituent elements in the drawings into one processor so as to realize the functions thereof.

Further, it is possible to realize any of the methods described in the above embodiments, by causing a computer such as a personal computer or a workstation to execute a program prepared in advance. The program may be provided as being incorporated, in advance, in a Read-Only Memory (ROM), a memory, or the like. Alternatively, the program may be provided as being stored in a computer-readable storage medium such as a Compact Disk Read-Only Memory (CD-ROM), a Flexible Disk (FD), a Compact Disk Recordable (CD-R), a Digital Versatile Disk (DVD), or the like, in a file in a format that is installable or executable by these devices. Further, the program may be stored in a computer connected to a network such as the Internet so as to be provided or distributed as being downloaded via the network. For example, the program is structured with modules including the functional units described later. In the actual hardware, as a result of a CPU reading and executing the program from a storage medium such as a ROM, the modules are loaded into a main storage device and generated in the main storage device.

According to at least one aspect of the embodiments described above, it is possible to efficiently proceed with the scan using the photon counting detector. In relation to the embodiments described above, the following notes are disclosed as certain aspects and selective characteristics of the present disclosure.

Note 1:
An X-ray CT apparatus including processing circuitry configured:
to obtain initial temperature information of a photon counting detector before a main scan, information about the shape of a subject, and a scan condition of the main scan;
to estimate a temperature change of the photon counting detector to be observed when the main scan is performed, on the basis of the initial temperature information, the information about the shape of the subject, and information about the scan condition of the main scan; and
to judge whether or not it is possible to perform the main scan, on the basis of the temperature change and the initial temperature information.

Note 2:
The information about the shape of the subject may be physique information including a body thickness of the subject.

Note 3:
The information about the shape of the subject may be obtained by using a position determining image, an optical image, a body shape model associated with the body shape information of the subject and the like.

Note 4:
On the basis of the information about the shape of the subject and the information about the scan condition of the main scan, the processing circuitry may estimate a heat generation amount of the photon counting detector to be observed when the main scan is performed. The Processing circuitry may estimate the temperature change on the basis of the initial temperature information and the heat generation amount.

Note 5:
The estimation of the heat generation amount may be based on a count rate output from the photon counting detector.

Note 6:
Further on the basis of information about an ambient temperature of the photon counting detector, the processing circuitry may estimate a heat generation amount of the photon counting detector to be observed when the main scan is performed. The processing circuitry may estimate the temperature change on the basis of the initial temperature information and the heat generation amount.

Note 7:
On the basis of the initial temperature information and a temperature increase value based on the heat generation amount, the processing circuitry may estimate a temperature of the photon counting detector to be observed when the main scan is performed.

Note 8:
The processing circuitry may compare a post-change temperature of the photon counting detector with a threshold value. When the post-change temperature does not exceed the threshold value, the processing circuitry may determine that the main scan is to be performed.

Note 9:
When a judgment result indicates that it is impossible to perform the main scan, the processing circuitry may calculate a waiting period until the photon counting detector reaches a temperature at which it is possible to perform the main scan.

Note 10:
The processing circuitry may calculate the waiting period further on the basis of information about an ambient temperature of the photon counting detector.

Note 11:
The display may display information about the waiting period.

Note 12:
The processing circuitry may further obtain information about a waiting period until an X-ray tube reaches a temperature at which it is possible to perform the main scan, and
the display may display information about the longer of two waiting periods, namely, the waiting period until the photon counting detector reaches the temperature at which it is possible to perform the main scan and the waiting period until the X-ray tube reaches the temperature at which it is possible to perform the main scan.

Note 13:
The processing circuitry may further obtain information about a waiting period until an X-ray tube reaches a temperature at which it is possible to perform the main scan. The processing circuitry may judge whether or not it is possible to perform the main scan at the time of obtaining the initial temperature information, on the basis of the temperature change of the photon counting detector and the waiting period until the X-ray tube reaches the temperature at which it is possible to perform the main scan.

Note 14:
When a judgment result indicates that it is impossible to perform the main scan, the processing circuitry may re-set the scan condition of the main scan.

Note 15:
The processing circuitry may further obtain temperature information of the photon counting detector from during the main scan. When a temperature of the photon counting detector would exceed a threshold value, the processing circuitry may judge whether or not the main scan is to be continued on the basis of a time period until the end of the main scan.

Note 16:
When the time period until the end of the main scan exceeds a threshold value, the processing circuitry may determine that one of the following is to be executed: changing the scan condition; stopping a part of operations of the photon counting detector; and cancelling the main scan.

Note 17:
On the basis of one or both of a temperature increase tendency of the photon counting detector and a medical examination detail of the main scan, the processing circuitry may determine that the one of the following is to be executed: changing the scan condition; stopping the part of the operations of the photon counting detector; and cancelling the main scan.

Note 18:
The processing circuitry may further obtain position information of the subject. The processing circuitry may judge whether or not there is a misalignment between a center position of the examined subject and a center of a field of view. A display may display information about the misalignment of positions, when the center position of the examined subject is misaligned with the center of the field of view.

Note 19:
The processing circuitry may move the position of the subject, on the basis of a misalignment amount of the center position of the examined subject from the center of the field of view.

Note 20:
The processing circuitry may move the position of the subject by driving at least one of table and tabletop.

Note 21:
The processing circuitry may estimate a temperature of the photon counting detector based on position information of the subject after movement.

Note 22:
The processing circuitry may obtain the initial temperature information on the basis of a count rate of the photon counting detector during a position determining scan or a temperature sensor.

Note 23:
An X-ray CT apparatus including:
processing circuitry configured:
to obtain position information of a subject with respect to a photon counting detector;
to judge whether or not there is a misalignment between a center position of the examined subject and a center of a field of view; and
a display configured to display information about the misalignment of positions when the center position of the examined subject is misaligned with the center of the field of view.

Note 24:
A storage medium storing therein, in a non-transitory manner, a program configured to cause a computer to execute:
an obtaining step of obtaining initial temperature information of a photon counting detector before a main scan, information about a shape of a subject, and a scan condition of the main scan;
an estimating step of estimating a temperature change of the photon counting detector to be observed when the main scan is performed, on a basis of the initial temperature information, the information about the shape of the subject, and information about the scan condition of the main scan; and
a judging step of judging whether or not it is possible to perform the main scan, on a basis of the temperature change and the initial temperature information.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray CT apparatus comprising processing circuitry configured:
to obtain initial temperature information of a photon counting detector before a main scan, information about a shape of a subject, and a scan condition of the main scan;
to estimate a temperature change of the photon counting detector to be observed when the main scan is performed, on a basis of the initial temperature information, the information about the shape of the subject, and information about the scan condition of the main scan; and
to judge whether or not it is possible to perform the main scan, on a basis of the temperature change and the initial temperature information.

2. The X-ray CT apparatus according to claim 1, wherein
on the basis of the information about the shape of the subject and the information about the scan condition of the main scan, the processing circuitry estimates a heat generation amount of the photon counting detector to be observed when the main scan is performed, and
the processing circuitry estimates the temperature change on the basis of the initial temperature information and the heat generation amount.

3. The X-ray CT apparatus according to claim 2, wherein
further on a basis of information about an ambient temperature of the photon counting detector, the processing circuitry estimates a heat generation amount of the photon counting detector to be observed when the main scan is performed, and
the processing circuitry estimates the temperature change on the basis of the initial temperature information and the heat generation amount.

4. The X-ray CT apparatus according to claim 2, wherein, on a basis of the initial temperature information and a temperature increase value based on the heat generation amount, the processing circuitry estimates a temperature of the photon counting detector to be observed when the main scan is performed.

5. The X-ray CT apparatus according to claim 1, wherein
the processing circuitry compares a post-change temperature of the photon counting detector with a threshold value, and
when the post-change temperature does not exceed the threshold value, the processing circuitry determines that the main scan is to be performed.

6. The X-ray CT apparatus according to claim 1, wherein, when a judgment result indicates that it is impossible to perform the main scan at the time, the processing circuitry calculates a waiting period until the photon counting detector reaches a temperature at which it is possible to perform the main scan.

7. The X-ray CT apparatus according to claim 6, wherein the processing circuitry calculates the waiting period further on a basis of information about an ambient temperature of the photon counting detector.

8. The X-ray CT apparatus according to claim 6, further comprising: a display configured to display information about the waiting period.

9. The X-ray CT apparatus according to claim 8, wherein
the processing circuitry further obtains information about a waiting period until an X-ray tube reaches a temperature at which it is possible to perform the main scan, and
the display displays information about a longer of two waiting periods, namely, the waiting period until the photon counting detector reaches the temperature at which it is possible to perform the main scan and the waiting period until the X-ray tube reaches the temperature at which it is possible to perform the main scan.

10. The X-ray CT apparatus according to claim 1, wherein
the processing circuitry further obtains information about a waiting period until an X-ray tube reaches a temperature at which it is possible to perform the main scan, and
the processing circuitry judges whether or not it is possible to perform the main scan at the time of obtaining the initial temperature information, on a basis of the temperature change of the photon counting detector and the waiting period until the X-ray tube reaches the temperature at which it is possible to perform the main scan.

11. The X-ray CT apparatus according to claim 1, wherein, when a judgment result indicates that it is impossible to perform the main scan at the time, the processing circuitry re-sets the scan condition of the main scan.

12. The X-ray CT apparatus according to claim 1, wherein
the processing circuitry further obtains temperature information of the photon counting detector from during the main scan, and
when a temperature of the photon counting detector would exceed a threshold value, the processing circuitry judges whether or not the main scan is to be continued on a basis of a time period until an end of the main scan.

13. The X-ray CT apparatus according to claim 12, wherein, when the time period until the end of the main scan exceeds a threshold value, the processing circuitry determines that one of the following is to be executed: changing the scan condition; stopping a part of operations of the photon counting detector; and cancelling the main scan.

14. The X-ray CT apparatus according to claim 13, wherein on a basis of one or both of a temperature increase tendency of the photon counting detector and a medical examination detail of the main scan, the processing circuitry determines that the one of the following is to be executed: changing the scan condition; stopping the part of the operations of the photon counting detector; and cancelling the main scan.

15. The X-ray CT apparatus according to claim 1, wherein
the processing circuitry further obtains position information of the subject,
the processing circuitry judges whether or not there is a misalignment between a center position of the subject and a center of a field of view, and
the X-ray CT apparatus further comprises a display configured to display information about the misalignment of positions, when the center position of the subject is misaligned with the center of the field of view.

16. The X-ray CT apparatus according to claim 15, wherein the processing circuitry moves a position of the subject, on a basis of a misalignment amount of the center position of the subject from the center of the field of view.

17. The X-ray CT apparatus according to claim 1, wherein the processing circuitry obtains the initial temperature information on a basis of a count rate of the photon counting detector during a position determining scan or a temperature sensor.

18. An X-ray CT apparatus comprising:
a processing circuitry configured to obtain position information of a subject with respect to a photon counting detector and to judge whether or not there is a misalignment between a center position of the subject and a center of a field of view; and a display configured to display information about the misalignment of positions when the center position of the subject is misaligned with the center of the field of view.

19. A storage medium storing therein, in a non-transitory manner, a program configured to cause a computer to execute:

an obtaining step of obtaining initial temperature information of a photon counting detector before a main scan, information about a shape of a subject, and a scan condition of the main scan;

an estimating step of estimating a temperature change of the photon counting detector to be observed when the main scan is performed, on a basis of the initial temperature information, the information about the shape of the subject, and information about the scan condition of the main scan; and a judging step of judging whether or not it is possible to perform the main scan, on a basis of the temperature change and the initial temperature information.

* * * * *